(12) United States Patent
Tsukamoto et al.

(10) Patent No.: US 12,343,555 B2
(45) Date of Patent: Jul. 1, 2025

(54) LIGHT IRRADIATION SYSTEM, CATHETER, AND LIGHT IRRADIATION DEVICE

(71) Applicant: ASAHI INTECC CO., LTD., Seto (JP)

(72) Inventors: Toshihiko Tsukamoto, Seto (JP); Yuko Katsurada, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 636 days.

(21) Appl. No.: 17/515,035

(22) Filed: Oct. 29, 2021

(65) Prior Publication Data

US 2022/0047885 A1  Feb. 17, 2022

Related U.S. Application Data

(63) Continuation of application No. PCT/JP2020/016879, filed on Apr. 17, 2020.

(30) Foreign Application Priority Data

May 16, 2019 (JP) ................. 2019-092694

(51) Int. Cl.
*A61N 5/06* (2006.01)
*A61B 90/00* (2016.01)

(52) U.S. Cl.
CPC .......... *A61N 5/0601* (2013.01); *A61B 90/39* (2016.02); *A61B 2090/3966* (2016.02);
(Continued)

(58) Field of Classification Search
CPC .............. A61N 5/0601; A61N 5/062; A61N 2005/0602; A61N 2005/0626;
(Continued)

(56) References Cited

U.S. PATENT DOCUMENTS 5,409,483 A    4/1995  Campbell et al.
5,772,642 A *  6/1998  Ciamacco, Jr. ...... A61N 5/1002
                                              604/529
(Continued)

FOREIGN PATENT DOCUMENTS

CN    104884115 A    9/2015
EP     0993843 A2    4/2000
(Continued)

OTHER PUBLICATIONS

Makoto Mitsunaga, et al., "Cancer Cell-Selective in Vivo Near Infrared Photoimmunotherapy Targeting Specific Membrane Molecules", Nature Medicine, vol. 17(12), pp. 1685-1691, Jun. 1, 2012.
(Continued)

*Primary Examiner* — Gary Jackson
*Assistant Examiner* — Skylar Lindsey Christianson
(74) *Attorney, Agent, or Firm* — Oliff PLC

(57) ABSTRACT

A light irradiation system for medical use includes a catheter having an elongated tube shape and a light irradiation device having an elongated shape and configured to be inserted into the catheter. The catheter includes a light transmitting portion provided at least in a part of a side surface on a distal end side of the catheter and configured to transmit light inside the catheter to outside of the catheter, and a first marker portion being radiopaque and being provided close to the light transmitting portion. The light irradiation device includes a light irradiation portion provided at least in a part of a side surface on a distal end side of the light irradiation device and configured to output irradiation light to the outside, and a second marker portion being radiopaque and being provided close to the light irradiation portion.

16 Claims, 29 Drawing Sheets

(52) U.S. Cl.
CPC ...... *A61N 2005/0602* (2013.01); *A61N 5/062* (2013.01); *A61N 2005/0626* (2013.01); *A61N 2005/063* (2013.01); *A61N 2005/0663* (2013.01)

(58) Field of Classification Search
CPC ...... A61N 2005/063; A61N 2005/0663; A61B 90/39; A61B 2090/3966
See application file for complete search history.

(56) References Cited

U.S. PATENT DOCUMENTS

| | | |
|---|---|---|
| 6,283,957 B1 | 9/2001 | Hashimoto et al. |
| 6,520,959 B1 | 2/2003 | Iwahashi et al. |
| 2008/0269846 A1 | 10/2008 | Burwell et al. |
| 2012/0330293 A1* | 12/2012 | Arai ............... A61N 5/062 606/15 |
| 2014/0235942 A1* | 8/2014 | Hellstrom ........... A61B 1/0615 128/200.26 |
| 2018/0008122 A1 | 1/2018 | Arai et al. |
| 2019/0099237 A1* | 4/2019 | Booker ............... A61B 5/0066 |

FOREIGN PATENT DOCUMENTS

| | | |
|---|---|---|
| EP | 2540247 A1 | 1/2013 |
| JP | H07-308393 A | 11/1995 |
| JP | H11-276605 A | 10/1999 |
| JP | H11-276606 A | 10/1999 |
| JP | H11-332876 A | 12/1999 |
| JP | H11-332877 A | 12/1999 |
| JP | 2001509038 A | 7/2001 |
| JP | 2005287832 A | 10/2005 |
| JP | 2007528752 A | 10/2007 |
| JP | 4966640 B2 | 7/2012 |
| JP | 2012515603 A | 7/2012 |
| JP | 2014523907 A | 9/2014 |
| JP | 5753573 B2 | 7/2015 |
| JP | 2018000867 A | 1/2018 |
| WO | 9729803 A1 | 8/1997 |
| WO | 2005007216 A2 | 1/2005 |
| WO | 2007084608 A2 | 7/2007 |
| WO | 2010086849 A1 | 8/2010 |
| WO | 2011/105631 A1 | 9/2011 |
| WO | 2013009475 A1 | 1/2013 |
| WO | 2014102599 A1 | 7/2014 |

OTHER PUBLICATIONS

Kazuhide Sato et al., "Spatially Selective Depletion of Tumor-Associated Regulatory T Cells With Near-Infrared Photoimmunotherapy", Science Translational Medicine, vol. 8, Issue 352, pp. 1-12, Aug. 17, 2016.

Shuhei Okuyama et al., "Interstitial Near-Infrared Photoimmunotherapy: Effective Treatment Areas and Light Doses Needed for Use With Fiber Optic Diffusers", Oncotarget, vol. 9, No. 13, pp. 11159-11169, Feb. 16, 2018.

* cited by examiner

Fig. 9

| No. | TARGET | EXAMPLE | TARGET | EXAMPLE |
|---|---|---|---|---|
| 1 | ENTIRE CIRCUMFERENCE | LIGHT TRANSMITTING PORTION 139 | PARTIAL CIRCUMFERENCE | LIGHT IRRADIATION PORTION 239 |
| 2 | PARTIAL CIRCUMFERENCE | LIGHT TRANSMITTING PORTION 139A | ENTIRE CIRCUMFERENCE | LIGHT IRRADIATION PORTION 239A |
| 3 | ENTIRE CIRCUMFERENCE | LIGHT TRANSMITTING PORTION 139 | ENTIRE CIRCUMFERENCE | LIGHT IRRADIATION PORTION 239A |
| 4 | PARTIAL CIRCUMFERENCE | LIGHT TRANSMITTING PORTION 139A | PARTIAL CIRCUMFERENCE | LIGHT IRRADIATION PORTION 239 |

Fig. 17
(A)
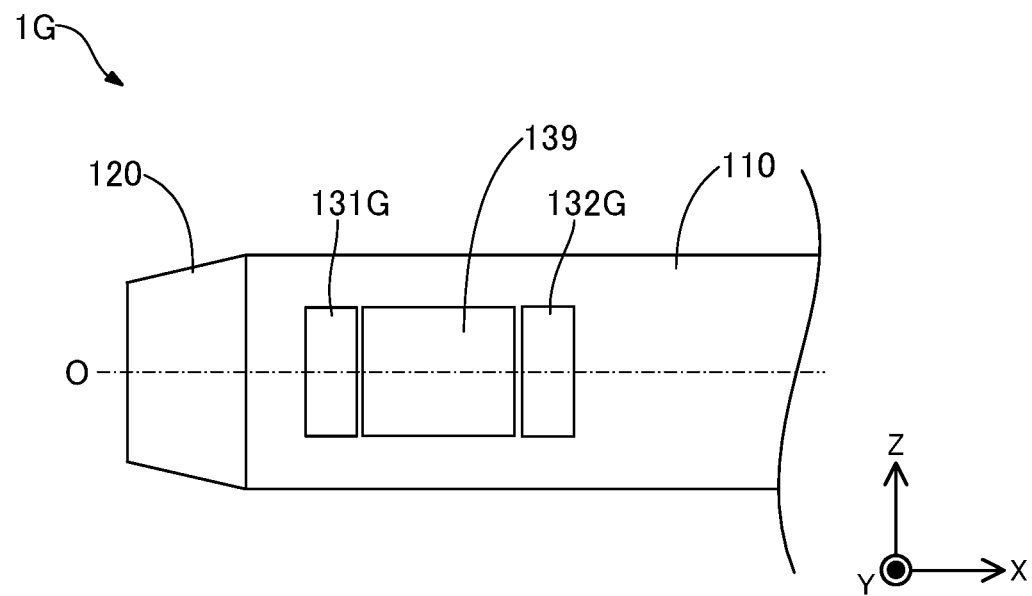
(B)
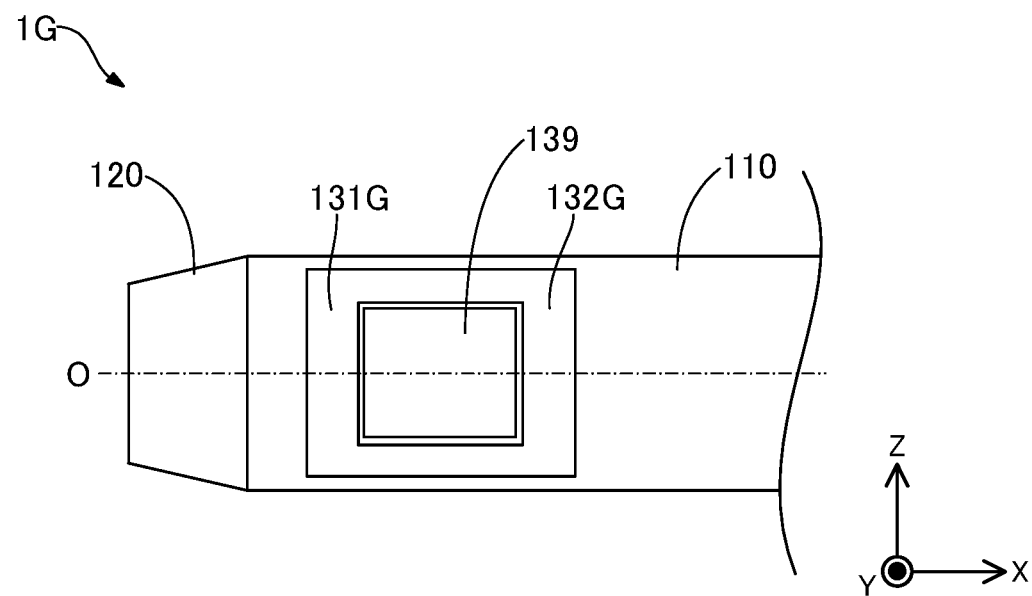

LIGHT IRRADIATION SYSTEM, CATHETER, AND LIGHT IRRADIATION DEVICE

The present application is a Bypass Continuation of PCT/JP2020/016879, filed Apr. 17, 2020, which is based upon and claims priority from JP Application No. 2019-092694 filed on May 16, 2019, the entirety of the prior applications being hereby incorporated by reference into this application.

TECHNICAL FIELD

The disclosed embodiments relate to a light irradiation system, a catheter, and a light irradiation device.

BACKGROUND ART

In cancer treatment, surgical, radiological, and pharmacological (chemical) methods are used alone or in combination, and development of each of these techniques is progressing in recent years. However, there are many cancers for which a satisfactory treatment technique has not yet been found, and further development of the treatment techniques is expected. A method called photodynamic therapy (PDT) is known as one of these cancer treatment techniques. In PDT, a photosensitizer is administered intravenously and then irradiated with light, to generate reactive oxygen in cancer cells and kill the cancer cells (see, for example, Non-Patent Literature 1). However, in PDT, the photosensitizer is accumulated with low selectivity in the cancer cells, so that the magnitude of the side effects caused by the uptake of the photosensitizer into normal cells is an issue and thus, PDT is not widely used as a treatment technique.

Therefore, a treatment technique that is attracting attention in recent years is near-infrared photoimmunotherapy (NIR-PIT). NIR-PIT uses a conjugate in which two compounds, an antibody against a specific antigen of cancer cells and a photosensitizer (for example, IRDye 700DX), are bound. When administered intravenously, this conjugate selectively accumulates in cancer cells in the body. Subsequently, if irradiation with light having an excitation wavelength (for example, 690 nm) of the photosensitizer in the conjugate is performed, the conjugate is activated and exhibits an anticancer effect (see, for example, Patent Literature 1). Selective accumulation of antibodies in the cancer and local light irradiation in NIR-PIT allow for reduction of side effects compared to PDT. Further, in NIR-PIT, irradiation with light in the near-infrared region of 690 nm (NIR irradiation) is performed, for example, and thus, an effect of the NIR irradiation on the immune system can also be expected (see, for example, Non-Patent Literature 2).

A certain wavelength region including the 690 nm region of the example described above is also called a spectroscopic window of a living body. Although light in this wavelength region is absorbed less by biological components than light in other wavelength regions, the light does not sufficiently penetrate when light irradiation is performed from the body surface, and thus, there is a problem in that NIR-PIT cannot be applied to cancers deep inside the body. Therefore, in recent years, research is being conducted on NIR-PIT in which light irradiation is performed at a position closer to the cancer cells, instead of light irradiation from the body surface (see, for example, Non-Patent Literature 3). For example, Patent Literature 2 and Patent Literature 3 disclose devices that can be used in such PDT and NIR-PIT. Both of the devices described in Patent Literature 2 and Patent Literature 3 are inserted into a blood vessel to be used and can be used to perform light irradiation deep inside the body.

CITATION LIST

Patent Literature

Patent Literature 1: Japanese Unexamined Patent Application Publication (Translation of PCT Application) No. 2014-523907
Patent Literature 2: Japanese Unexamined Patent Application Publication No. 2018-867
Patent Literature 3: Japanese Unexamined Patent Application Publication (Translation of PCT Application) No. 2007-528752

Non-Patent Literature

Non-Patent Literature 1: Makoto Mitsunaga, Mikako Ogawa, Nobuyuki Kosaka Lauren T. Rosenblum, Peter L. Choyke, and Hisataka Kobayashi, Cancer Cell-Selective In Vivo Near Infrared Photoimmunotherapy Targeting Specific Membrane Molecules, Nature Medicine 2012 17(12), p. 1685-1691
Non-Patent Literature 2: Kazuhide Sato, Noriko Sato, Biying Xu, Yuko Nakamura, Tadanobu Nagaya, Peter L. Choyke, Yoshinori Hasegawa, and Hisataka Kobayashi, Spatially selective depletion of tumor-associated regulatory T cells with near-infrared photoimmunotherapy, Science Translational Medicine 2016 Vol. 8 Issue352, ra110
Non-Patent Literature 3: Shuhei Okuyama, Tadanobu Nagaya, Kazuhide Sato, Fusa Ogata, Yasuhiro Maruoka, Peter L. Choyke, and Hisataka Kobayashi, Interstitial near-infrared photoimmunotherapy: effective treatment areas and light doses needed for use with fiber optic diffusers, Oncotarget 2018 Feb. 16; 9(13), p. 11159-11169

SUMMARY

Technical Problem

Here, in PDT and NIR-PIT, as described above, the cancer cells in which the conjugate is accumulated are irradiated with light of the excitation wavelength of the photosensitizer in the conjugate to kill the cancer cells. On the other hand, it is preferable to avoid light irradiation to normal cells other than cancer cells to reduce the risk of cell damage. Therefore, in the techniques described in Patent Literature 2 and Patent Literature 3, it is difficult to position a light irradiation portion in the blood vessel, and thus, there is a problem in that it is not possible to selectively irradiate with light a site where the cancer cells are present.

It is noted that this problem is not limited to PDT and NIR-PIT, and is common to all devices used in examinations or treatments including a light irradiation process in the body. Further, these problems are not limited to devices inserted into a blood vessel, and are common to all devices inserted into living body lumens, such as the vascular system, the lymphatic system, the biliary system, the urinary system, the respiratory system, the digestive system, secretory glands, and reproductive organs.

The disclosed embodiments have been contrived to solve at least a part of the above-mentioned problems, and an object of the disclosed embodiments is to provide a light irradiation system, a catheter, and a light irradiation device capable of selectively irradiating a specific position in a living body lumen with light.

Solution to Problem

The disclosed embodiments have been made to solve at least a part of the above-described problems, and can be implemented as the following aspects.
(1) According to one aspect of the disclosed embodiments, a light irradiation system for medical use is provided. The light irradiation system includes a catheter having an elongated tube shape, and a light irradiation device having an elongated shape and being inserted into the catheter to be used. The catheter includes a light transmitting portion provided at least in a part of a side surface on a distal end side of the catheter and transmitting light inside the tube to an outside, and a first marker portion being radiopaque and being provided close to the light transmitting portion. The light irradiation device includes a light irradiation portion provided at least in a part of a side surface on a distal end side of the light irradiation device and outputting irradiation light to the outside, and a second marker portion being radiopaque and being provided close to the light irradiation portion.

According to this configuration, the catheter and the light irradiation device include the first and second marker portions being radiopaque and being provided close to the light transmitting portion and the light irradiation portion, and thus, the operator can observe the positions of the first and second marker portions in the body by X-ray imaging, and easily position a light irradiation portion (the light transmitting portion and the light irradiation portion) in the living body lumen. Therefore, according to the present light irradiation system, it is possible to selectively irradiate a specific position in the living body lumen with light, for example, cancer cells can be selectively irradiated with light in NIR-PIT. Further, the first marker portion is provided close to the light transmitting portion, and the second marker portion is provided close to the light irradiation portion. Therefore, when using the light irradiation system, after inserting the light irradiation device into the catheter, the operator can observe the positional relationship between the first marker portions and the second marker portions by X-ray imaging, and thus easily achieve alignment between the light transmitting portion and the light irradiation portion. Further, the catheter and the light irradiation device are separately provided, and thus, the degree of freedom in designing the device can be improved and the range of procedures can be expanded.
(2) In the light irradiation system of the aspect described above, the first marker portion may be provided at least at two locations including locations on a distal end side and a proximal end side of the light transmitting portion in an axial direction of the catheter. According to this configuration, the first marker portion is provided at least at two locations, that is, at the distal end side and the proximal end side of the light transmitting portion, and thus, it is possible to more easily achieve alignment between the light transmitting portion and the light irradiation portion.
(3) In the light irradiation system of the aspect described above, the second marker portion may be provided at least at two locations including locations on a distal end side and a proximal end side of the light irradiation portion in an axial direction of the light irradiation device. According to this configuration, the second marker portion is provided at least at two locations, that is, at the distal end side and the proximal end side of the light irradiation portion, and thus, it is possible to more easily achieve alignment between the light transmitting portion and the light irradiation portion.
(4) In the light irradiation system of the aspect described above, in a state where the light irradiation device is inserted into the catheter and the light transmitting portion is aligned with the light irradiation portion in an axial direction of the light irradiation system, the first marker portion at the distal end side may be distal to the second marker portion at the distal end side, in the axial direction, and the first marker portion at the proximal end side may be proximal to the second marker portion at the proximal end side, in the axial direction. According to this configuration, in a state where the light irradiation device is inserted into the catheter and the light transmitting portion is aligned with the light irradiation portion, the first marker portion at the distal end side is distal to the second marker portion at the distal end side, in the direction of the axis, and the first marker portion at the proximal end side is proximal to the second marker portion at the proximal end side, in the direction of the axis. In other words, in the state where the light transmitting portion is aligned with the light irradiation portion, the first marker portions of the catheter are located on both ends of the second marker portions of the light irradiation device interposed between the first marker portions, and thus it becomes easy to intuitively grasp the positional relationship between the light transmitting portion and the light irradiation portion.
(5) In the light irradiation system of the aspect described above, the first marker portion may have a shape surrounding the catheter in a circumferential direction, and the second marker portion may have a shape surrounding the light irradiation device in a circumferential direction. According to this configuration, the first and second marker portions have shapes surrounding the catheter and the light irradiation device, respectively, in the circumferential direction, and thus, it is possible to easily grasp an orientation of the catheter and the light irradiation device in the living body lumen. Therefore, it is possible to easily and highly accurately achieve alignment between the light transmitting portion and the light irradiation portion.
(6) In the light irradiation system of the aspect described above, a plurality of sets of the light transmitting portion and the first marker portion may be provided in the catheter in the axial direction of the catheter. According to this configuration, the catheter is provided with a plurality of sets of the light transmitting portion and the first marker portion. Therefore, it is possible to irradiate different regions in the axial direction of the catheter with light by moving only the light irradiation device in the axial direction inside the catheter without moving the catheter. Further, the first marker portion is provided in each of the plurality of light transmitting portions, and thus, it is possible to easily achieve alignment between the light irradiation portion and each of the light transmitting portions.
(7) In the light irradiation system of the aspect described above, the catheter may further include a distal tip joined to a distal end side of the catheter, and the distal tip may be formed with a through-hole penetrating the distal tip in the axial direction of the catheter and having a diameter smaller than an outer diameter of the light irradiation device. According to this configuration, the through-hole is formed in the distal tip joined to the distal end side of the catheter, and thus, the catheter can be easily delivered to a target site in the living body lumen by inserting a guide wire from the through-hole. Further, the diameter of the through-hole is smaller than the outer diameter of the light irradiation device, and thus, when the light irradiation device is inserted into the catheter, a distal end of the light irradiation device can abut against the distal tip, to prevent the light irradiation device from being advanced beyond the distal end of the catheter.

(8) In the light irradiation system of the aspect described above, the catheter may further include a temperature sensor measuring a temperature at least in a vicinity of the light transmitting portion. According to this configuration, the temperature sensor measuring the temperature at least in the vicinity of the light transmitting portion is provided, and thus, it is possible to observe in real time a temperature change in living tissue due to the light irradiation, which can contribute to the suppression of blood coagulation and damage of living tissue due to the light irradiation.

(9) In the light irradiation system of the aspect described above, the light irradiation portion may be a light transmitting body transmitting emission light from a core exposed in a part of an optical fiber on a distal end side. According to this configuration, the light irradiation portion can be easily formed by utilizing an optical fiber. Further, the core of the optical fiber is covered with the light transmitting body, and thus, it is possible to suppress a decrease in the strength of the optical fiber in the exposed part of the core.

(10) According to one aspect of the disclosed embodiments, a catheter is provided. The catheter has an elongated tube shape, and includes a light transmitting portion provided at least in a part of a side surface on a distal end side of the catheter and transmitting light inside the tube to an outside, and a first marker portion being radiopaque and being provided close to the light transmitting portion. According to this configuration, the catheter includes the first marker portion being radiopaque and being provided close to light transmitting portion, and thus, the operator can observe the position of the first marker portion in the body by X-ray imaging, and easily position the light transmitting portion in the living body lumen.

(11) According to one aspect of the disclosed embodiments, a light irradiation device is provided. The light irradiation device has an elongated shape, and includes a light irradiation portion provided at least in a part of a side surface on a distal end side of the light irradiation device and outputting irradiation light to the outside, and a second marker portion being radiopaque and being provided close to the light irradiation portion. According to this configuration, the light irradiation device includes the second marker portion being radiopaque and being provided close to light irradiation portion, and thus, the operator can observe the position of the second marker portion in the body by X-ray imaging, and easily position the light irradiation portion in the living body lumen.

It is noted that the disclosed embodiments can be realized in various aspects, for example, the disclosed embodiments can be realized by aspects such as a catheter, a light irradiation device, a light irradiation system in which the catheter and the light irradiation device are provided separately or integrally, and a manufacturing method of the catheter, the light irradiation device, and the light irradiation system.

BRIEF DESCRIPTION OF DRAWINGS

FIG. 9 is an explanatory table showing combinations of a light transmitting portion and a light irradiation portion.

FIG. 17 is an explanatory diagram illustrating a configuration of a catheter of the eighth embodiment.

DETAILED DESCRIPTION OF EMBODIMENTS

First Embodiment

Figure 1:
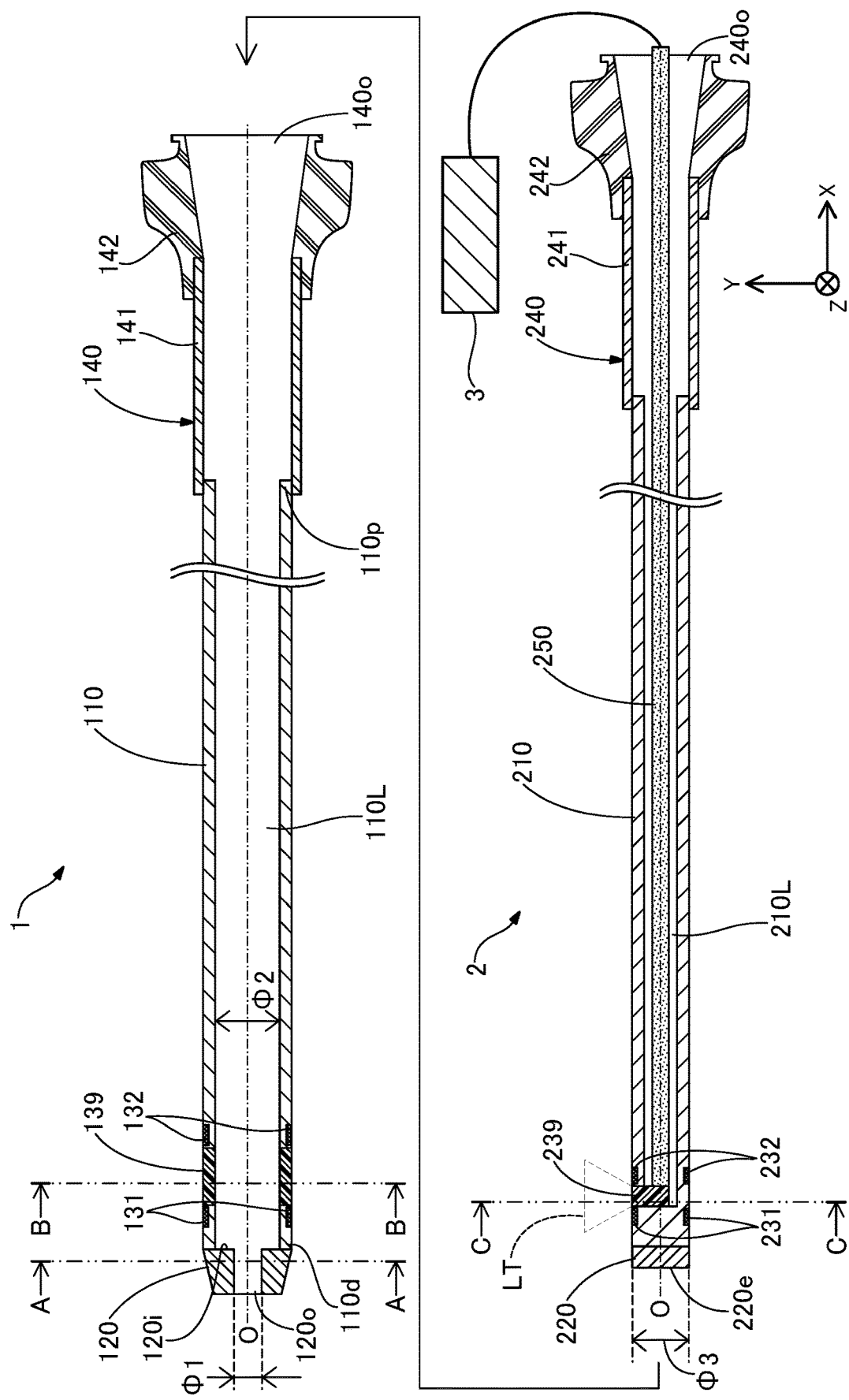
FIG. 1 is an explanatory diagram illustrating a configuration of a light irradiation system of a first embodiment.

FIG. 1 is an explanatory diagram illustrating a configuration of a light irradiation system of a first embodiment. The light irradiation system is a system that is inserted into a living body lumen such as the vascular system, the lymphatic system, the biliary system, the urinary system, the respiratory system, the digestive system, secretory glands, and reproductive organs to be used, and irradiates living tissue with light, from inside the living body lumen. The light irradiation system can be used in photodynamic therapy (PDT) and near-infrared photoimmunotherapy (NIR-PIT), for example. In the following embodiments, laser light is described as an example of light, but the light being used is not limited to the laser light and the light irradiation system may have a configuration in which LED light or white light is used, for example. The light irradiation system includes a catheter 1 and a light irradiation device 2 that is inserted into the catheter 1 to be used. In FIG. 1, the catheter 1 and the light irradiation device 2 are illustrated separately.

In FIG. 1, an axis passing through a center of the catheter 1 and an axis passing through a center of the light irradiation device 2 are represented by an axis O (dash-dot-dash line). Hereinafter, in a state where the light irradiation device 2 is inserted into the catheter 1, it is assumed that axes passing through the centers of the light irradiation device 2 and the catheter 1 coincide with the axis O, but the axes passing through the centers of the light irradiation device 2 and the catheter 1 when the light irradiation device 2 is inserted into the catheter 1 may be different from each other. Further, in FIG. 1, an X-axis, a Y-axis, and a Z-axis that are orthogonal to each other are illustrated. The X-axis corresponds to an axial direction of the catheter 1 and the light irradiation device 2, the Y-axis corresponds to a height direction of the catheter 1 and the light irradiation device 2, and the Z-axis corresponds to a width direction of the catheter 1 and the light irradiation device 2. The left side (a −X-axis direction) in FIG. 1 is referred to as a "distal end side" of the catheter 1, the light irradiation device 2, and each constitution component, and the right side (a +X-axis direction) in FIG. 1 is referred to as a "proximal end side" of the catheter 1, the light irradiation device 2, and each constitution component. End portions of the catheter 1, the light irradiation device 2, and each constitution component located on the distal end side are referred to as a "distal end", and the distal end and a vicinity thereof are referred to as a "distal end portion". Further, end portions of the catheter 1, the light irradiation device 2, and each constitution component located on the proximal end side are referred to as a "proximal end", and the proximal end and a vicinity thereof are referred to as a "proximal end portion". The distal end side corresponds to a "distal side" inserted into a living body, and the proximal end side corresponds to a "proximal side" operated by an operator such as a doctor. These features are common to each drawing after FIG. 1 illustrating an overall configuration.

The catheter 1 has an elongated tube shape and includes a shaft 110, a distal tip 120, and a connector 140. The shaft 110 is an elongated member extending along the axis O. The shaft 110 has a substantially hollow cylindrical shape and both ends of the shaft 110, i.e., a distal end portion 110d and a proximal end portion 110p, are open. The shaft 110 includes a lumen 110L inside the shaft 110. The lumen 110L functions as a guide wire lumen for inserting a guide wire through the catheter 1 during delivery of the catheter 1. The lumen 110L functions as a device lumen for inserting the light irradiation device 2 into the catheter 1 after the delivery of the catheter 1. Using a single lumen as both the guide wire lumen and the device lumen, as described above, makes it possible to reduce the diameter of the catheter 1. The shaft 110 may have any outer diameter, inner diameter, and length.

Figure 2:
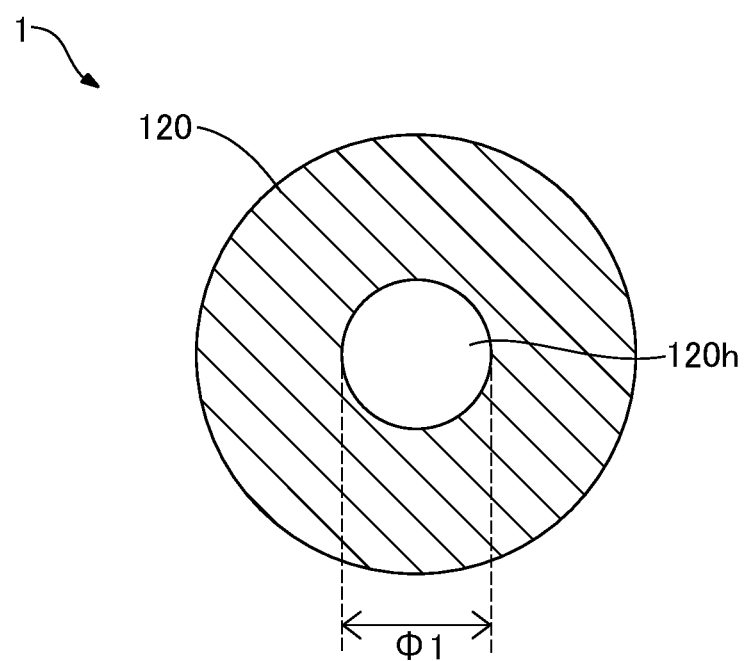
FIG. 2 is an explanatory diagram illustrating a cross-sectional configuration taken along line A-A of FIG. 1.

FIG. 2 is an explanatory diagram illustrating a cross-sectional configuration taken along line A-A of FIG. 1. The distal tip 120 is a member that is joined to the distal end portion of the shaft 110 and advances in a living body lumen ahead of other members. As illustrated in FIG. 1, to facilitate the progress of the catheter 1 in the living body lumen, the distal tip 120 has an outer shape with diameter that decreases from the proximal end side to the distal end side. Further, as illustrated in FIG. 2, a through-hole 120h penetrating the distal tip 120 in a direction of the axis O is formed in a substantially central part of the distal tip 120. Here, a diameter phi 1 of the through-hole 120h is smaller than a diameter phi 2 of the lumen 110L of the shaft 110. Therefore, as illustrated in FIG. 1, at a boundary between the shaft 110 and the distal tip 120, an inner surface 120i of the distal tip 120 protrudes and forms a step. An opening 120o of the distal tip 120 leads to the through-hole 120h and is used when inserting a guide wire (not illustrated) into the catheter 1. The distal tip 120 may have any outer diameter and length.

The connector 140 is a member arranged on the proximal end side of the catheter 1 and gripped by the operator. The connector 140 includes a connection portion 141 having a substantially cylindrical shape and a pair of blades 142. A distal end portion of the connection portion 141 is joined to the proximal end portion 110p of the shaft 110, and a proximal end portion of the connection portion 141 is joined to the blades 142. The blades 142 may have a structure that is integrally formed with the connector 140. An opening 140o of the connector 140 leads to the lumen 110L via the inside of the connector 140, and is used when inserting the light irradiation device 2 into the catheter 1. The connection portion 141 may have any outer diameter, inner diameter, and length, and the blades 142 may have any shape.

Figure 3:
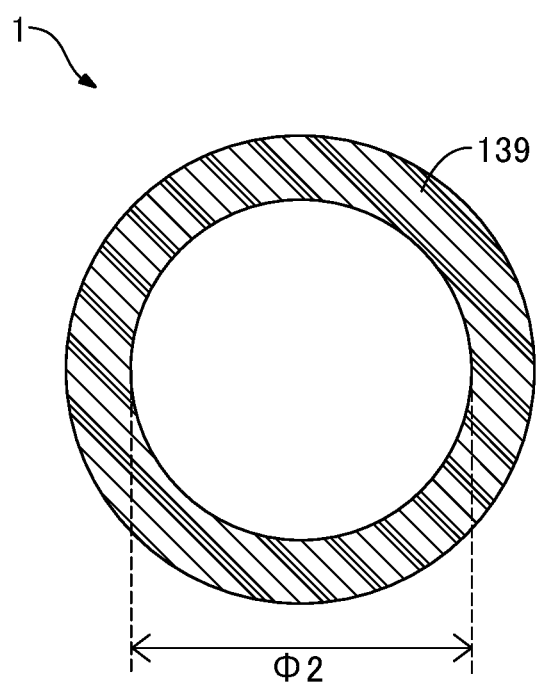
FIG. 3 is an explanatory diagram illustrating a cross-sectional configuration taken along line B-B of FIG. 1.

FIG. 3 is an explanatory diagram illustrating a cross-sectional configuration taken along line B-B of FIG. 1. The shaft 110 of the catheter 1 is further provided with a light transmitting portion 139 and first marker portions 131 and 132. The light transmitting portion 139 transmits light inside the shaft 110 to the outside. As illustrated in FIGS. 1 and 3, the light transmitting portion 139 is a hollow member having a substantially cylindrical shape, an outer diameter that is substantially the same as the outer diameter of the shaft 110, and an inner diameter that is substantially the same as the diameter phi 2 of the lumen 110L of the shaft 110. In other words, the light transmitting portion 139 is provided wholly in the circumferential direction, and wholly transmits light inside the shaft 110 to the outside in the circumferential direction. The light transmitting portion 139 is joined to the shaft 110 at each of the proximal end side and the distal end side. The light transmitting portion 139 can be formed of a transparent resin material having light-transmitting properties, such as an acrylic resin, polyethylene terephthalate, and polyvinyl chloride.

The first marker portions 131 and 132 function as marks indicating positions of the light transmitting portion 139.

The first marker portion 131 is provided close to the distal end portion of the light transmitting portion 139, and functions as a mark indicating a position of the distal end portion of the light transmitting portion 139. The first marker portion 132 is provided close to the proximal end portion of the light transmitting portion 139, and functions as a mark indicating a position of the proximal end portion of the light transmitting portion 139. The first marker portions 131 and 132 are hollow members each having a substantially hollow cylindrical shape. In the example of FIG. 1, the first marker portions 131 and 132 are respectively arranged in recess portions formed in an outer surface of the shaft 110 and are joined to the outer surface of the shaft 110. In other words, the first marker portions 131 and 132 are each embedded in the outer surface of the shaft 110 to surround the shaft 110 in a circumferential direction. It is noted that the first marker portions 131 and 132 may be joined to the outer surface of the shaft 110 without the recess portions, and may protrude from the outer surface of the shaft 110.

The light irradiation device 2 has an elongated shape and includes a shaft 210, a distal tip 220, and a connector 240. The shaft 210 is an elongated member extending along the axis O. The shaft 210 has a bottomed cylindrical shape having a closed distal end portion and an open proximal end portion. The shaft 210 includes a lumen 210L inside the shaft 210. An optical fiber 250 is inserted into and fixed to the lumen 210L. A proximal end portion of the optical fiber 250 is directly connected via a connector (not illustrated) or indirectly connected via another optical fiber, to a laser light generator 3 generating laser light of any wavelength. At a distal end portion of the optical fiber 250, a clad and a coating are removed from the optical fiber to expose a core of the optical fiber 250.

The distal tip 220 is a member that is joined to the distal end portion of the shaft 210 and advances ahead of other members in the lumen 110L of the catheter 1. As illustrated in FIG. 1, the distal tip 220 has a substantially columnar shape and has a diameter that is substantially the same as an outer diameter phi 3 of the shaft 210. Here, in the light irradiation device 2, it is preferable that the outer diameter phi 3 of the shaft 210 and the distal tip 220 is smaller than the diameter phi 2 of the lumen 110L of the shaft 110 and larger than the diameter phi1 of the through-hole 120h of the distal tip 120 (phi 1<phi 3<phi 2). The connector 240 is a member arranged on the proximal end side of the light irradiation device 2 and gripped by the operator. The connector 240 includes a connection portion 241 having a substantially cylindrical shape and a pair of blades 242. A distal end portion of the connection portion 241 is joined to a proximal end portion of the shaft 210, and a proximal end portion of the connection portion 241 is joined to the blades 242. The blades 242 may have a structure that is integrally formed with the connector 240.

Figure 4:
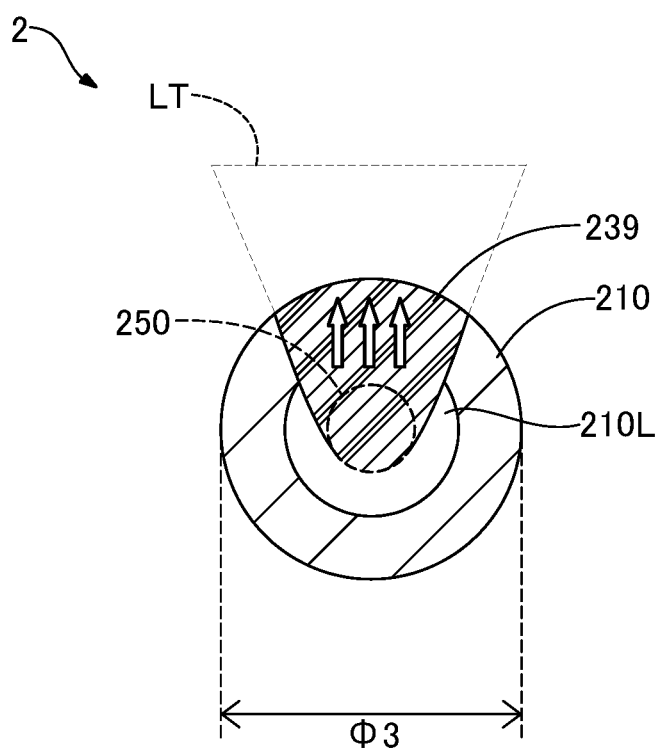
FIG. 4 is an explanatory diagram illustrating a cross-sectional configuration taken along line C-C of FIG. 1.

FIG. 4 is an explanatory diagram illustrating a cross-sectional configuration taken along line C-C of FIG. 1. The shaft 210 of the light irradiation device 2 is further provided with a light irradiation portion 239 and second marker portions 231 and 232. The light irradiation portion 239 outputs, for irradiation, emission light LT from the core exposed at the distal end portion of the optical fiber 250, to the outside in one direction (FIG. 4: white arrows) of a side surface of the light irradiation device 2. As illustrated in FIG. 4, the light irradiation portion 239 is a resin body that covers a distal end of the core of the optical fiber 250 and is provided to be exposed in a part of the side surface of the shaft 210. The light irradiation portion 239 can be formed, for example, by applying the light irradiation portion 239 to an acrylic ultraviolet-curable resin in which fine quartz powder is dispersed and curing the resin with ultraviolet light. It is noted that the light irradiation portion 239 may be realized in a different manner, and may be realized, for example, by a light-reflecting mirror, instead of the resin body. Further, the core exposed at the distal end portion of the optical fiber 250 may be subjected to a well-known process (for example, a process of diagonally cutting a distal end surface, a process of forming a notch, a sandblast process, and a chemical process), to form the light irradiation portion 239 in a part of the optical fiber 250.

Laser light LT generated by the laser light generator 3 is transmitted from the proximal end side to the distal end side of the optical fiber 250 via the core of the optical fiber, and is output, for irradiation, from the core exposed at the distal end portion via the light irradiation portion 239 to the outside, in one direction (FIG. 4: white arrows) of the side surface of the light irradiation device 2.

The second marker portions 231 and 232 function as marks indicating positions of the light irradiation portion 239. The second marker portion 231 is provided close to the distal end portion of the light irradiation portion 239, and functions as a mark indicating a position of the distal end portion of the light irradiation portion 239. The second marker portion 232 is provided close to the proximal end portion of the light irradiation portion 239, and functions as a mark indicating a position of the proximal end portion of the light irradiation portion 239. The second marker portions 231 and 232 are hollow members each having a substantially hollow cylindrical shape. In the example of FIG. 1, the second marker portions 231 and 232 are respectively arranged in recess portions formed in an outer surface of the shaft 210 and are joined to the outer surface of the shaft 210. In other words, the second marker portions 231 and 232 are each embedded in the outer surface of the shaft 210 to surround the shaft 210 in a circumferential direction. It is noted that the second marker portions 231 and 232 may be joined to the outer surface of the shaft 210 without the recess portions, and may protrude from the outer surface of the shaft 210.

The first marker portions 131 and 132 of the catheter 1 and the second marker portions 231 and 232 of the light irradiation device 2 can be formed of a radiopaque resin material or a radiopaque metal material. For example, when a resin material is used, the first marker portions 131 and 132 and the second marker portions 231 and 232 can be formed by using a mixture of a radiopaque material, such as bismuth trioxide, tungsten, or barium sulfate, and a resin material, such as a polyamide resin, a polyolefin resin, a polyester resin, a polyurethane resin, a silicon resin, or a fluororesin. When a metal material is used, for example, the first marker portions 131 and 132 and the second marker portions 231 and 232 can be formed of a radiopaque material such as gold, platinum, tungsten, or an alloy containing these elements (for example, a platinum-nickel alloy).

The shaft 110 of the catheter 1 and the shaft 210 of the light irradiation device 2 are preferably antithrombotic, flexible, and biocompatible, and can be formed of a resin material or a metal material. For example, a polyamide resin, a polyolefin resin, a polyester resin, a polyurethane resin, a silicon resin, a fluororesin, and the like can be employed as the resin material. For example, stainless steel such as SUS304, a nickel-titanium alloy, a cobalt-chromium alloy, tungsten steel and the like can be employed as the metal material. Further, the shaft 110 and the shaft 210 can be formed as a bonded structure in which a plurality of the above-mentioned materials are combined. The distal tip 120 of the catheter 1 and the distal tip 220 of the light irradiation device 2 are preferably flexible, and can be formed of, for example, a resin material such as polyurethane and a polyurethane elastomer. The connector 140 of the catheter 1 and the connector 240 of the light irradiation device 2 can be formed of a resin material such as a polyamide, polypropylene, a polycarbonate, polyacetal, and a polyether sulfone.

Figure 5:
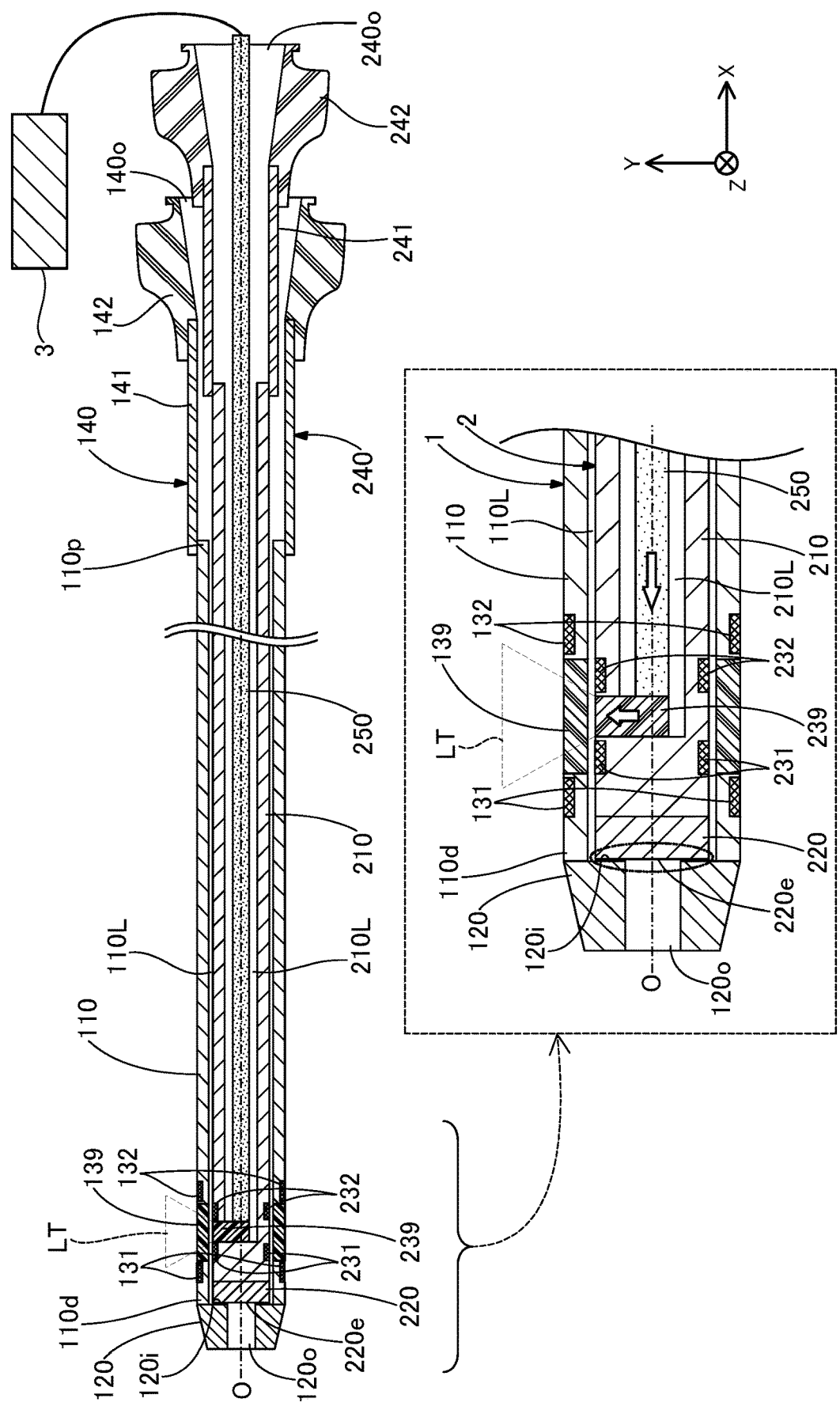
FIG. 5 is an explanatory diagram illustrating a usage state of the light irradiation system.

FIG. 5 is an explanatory diagram illustrating a usage state of the light irradiation system. The upper part of FIG. 5 illustrates a state where the light irradiation device 2 is inserted into the catheter 1. The lower part of FIG. 5 is an enlarged view of a part on the distal end side. A method of using the light irradiation system will be described with reference to FIGS. 1 and 5. First, an operator inserts a guide wire into a living body lumen. Next, the operator inserts a proximal end side of the guide wire from the opening 120o of the distal tip 120 of the catheter 1 illustrated in FIG. 1, through the lumen 110L so that the guide wire protrudes from the opening 140o of the connector 140. Subsequently, the operator pushes the catheter 1 into the living body lumen along the guide wire, and the light transmitting portion 139 of the catheter 1 is delivered to a target site for light irradiation (for example, in the case of NIR-PIT, a vicinity of a cancer cell). Thus, by inserting the guide wire from the through-hole 120h formed in the distal tip 120 of the catheter 1, the operator can easily deliver the catheter 1 to the target site in the living body lumen. It is noted that, during delivery, the operator can position the catheter 1 in the living body lumen, while observing, in an X-ray image, the positions of the first marker portions 131 and 132 arranged in the vicinity of the light transmitting portion 139. Afterwards, the surgeon removes the guide wire from the catheter 1.

Next, as illustrated in FIG. 5, the operator inserts the light irradiation device 2 from the opening 140o of the connector 140 of the catheter 1. The operator pushes the light irradiation device 2 toward the distal end side of the catheter 1, along the lumen 110L of the catheter 1. Here, as described above, if the outer diameter phi 3 of the light irradiation device 2 is smaller than the diameter phi 2 of the lumen 110L of the catheter 1 and larger than the diameter phi 1 of the through-hole 120h of the distal tip 120, a distal end surface 220e of the light irradiation device 2 abuts against the inner surface 120i of the distal tip 120 when the light irradiation device 2 is inserted into the catheter 1, and thus, it is possible to prevent the light irradiation device 2 from being advanced beyond the distal end of the catheter 1 (lower part of FIG. 5: round frame with dashed line).

After that, the operator aligns the light irradiation portion 239 with the light transmitting portion 139 in the direction of the axis O (X-axis direction), while observing, in an X-ray image, a positional relationship between the first marker portions 131 and 132 and the second marker portions 231 and 232. Thus, the laser light LT transmitted via the optical fiber 250 and emitted from the light irradiation portion 239 can be transmitted through the light transmitting portion 139 of the catheter 1 and emitted to living tissue on the outside. It is noted that, in the catheter 1 of the present embodiment, the light transmitting portion 139 is provided in the entire circumferential direction (FIG. 3). Therefore, in the light irradiation system of the present embodiment, the operator only needs to achieve alignment between the light transmitting portion 139 and the light irradiation portion 239 in the direction of the axis O (X-axis direction), and does not need to achieve alignment between the light transmitting portion 139 and the light irradiation portion 239 in the circumferential direction.

As described above, according to the light irradiation system of the first embodiment, the catheter 1 and the light irradiation device 2 include the first marker portions 131 and 132 and the second marker portions 231 and 232 which are radiopaque and are provided close to the light transmitting portion 139 and the light irradiation portion 239. Thus, the operator can observe the positions of the first marker portions 131 and 132 and the second marker portions 231 and 232 in the body by X-ray imaging, and thus easily position a light irradiation portion (the light transmitting portion 139 and the light irradiation portion 239) in the living body lumen. Therefore, according to the light irradiation system of the first embodiment, it is possible to selectively irradiate a specific position in the living body lumen with light, for example, cancer cells can be selectively irradiated with light in NIR-PIT.

Further, the first marker portions 131 and 132 are provided close to the light transmitting portion 139, and the second marker portions 231 and 232 are provided close to the light irradiation portion 239. Therefore, as illustrated in FIG. 5, when using the light irradiation system, after inserting the light irradiation device 2 into the catheter 1, the operator can observe the positional relationship between the first marker portions 131 and 132 and the second marker portions 231 and 232 by X-ray imaging, and thus easily achieve alignment between the light transmitting portion 139 and the light irradiation portion 239. Further, the catheter 1 and the light irradiation device 2 are separately provided, and thus, the degree of freedom in designing the device can be improved and the range of procedures can be expanded. Further, in the catheter 1, using the single lumen 110L as both the guide wire lumen and a lumen for the light irradiation device 2 makes it possible to reduce the diameter of the catheter 1.

Further, in the catheter 1, the first marker portions 131 and 132 are provided at two locations, that is, at the distal end side and the proximal end side of the light transmitting portion 139, and thus, the operator can more easily achieve alignment between the light transmitting portion 139 and the light irradiation portion 239. Similarly, in the light irradiation device 2, the second marker portions 231 and 232 are provided at two locations, that is, at the distal end side and the proximal end side of the light irradiation portion 239, and thus, the operator can more easily achieve alignment between the light transmitting portion 139 and the light irradiation portion 239.

Further, in the light irradiation system of the present embodiment, as illustrated in FIG. 5, in a state where the light irradiation device 2 is inserted into the catheter 1 and the light transmitting portion 139 is aligned with the light irradiation portion 239, the first marker portion 131 at the distal end side is distal to the second marker portion 231 at the distal end side, in the direction of the axis O, and the first marker portion 132 at the proximal end side is proximal to the second marker portion 232 at the proximal end side, in the direction of the axis O. In other words, in the light irradiation system of FIG. 5, in the state where the light transmitting portion 139 is aligned with the light irradiation portion 239, the first marker portions 131 and 132 of the catheter 1 are located on both ends of the second marker portions 231 and 232 of the light irradiation device 2 interposed between the first marker portions 131 and 132. Therefore, it is easy for the operator to intuitively grasp the positional relationship between the light transmitting portion 139 and the light irradiation portion 239.

Further, in the light irradiation system of the present embodiment, the first marker portions 131 and 132 and the second marker portions 231 and 232 have a shape that surrounds the catheter 1 and the light irradiation device 2 in the circumferential direction, and thus, it is possible to easily grasp an orientation of the catheter 1 and the light irradiation device 2 in the living body lumen by X-ray imaging. Therefore, the operator can easily and highly accurately achieve alignment between the light transmitting portion 139 and the light irradiation portion 239.

Further, in the light irradiation system of the present embodiment, the diameter phi 1 of the through-hole 120h of the catheter 1 is smaller than the outer diameter phi 3 of the light irradiation device 2. Therefore, as illustrated in FIG. 5, the distal end of the light irradiation device 2 abuts against the inner surface 120i of the distal tip 120 of the catheter 1 when the light irradiation device 2 is inserted into the catheter 1, and thus, it is possible to prevent the light irradiation device 2 from being advanced beyond the distal end of the catheter 1. Further, as illustrated in the lower part of FIG. 5, in a state where the light irradiation device 2 abuts against the catheter 1, the light transmitting portion 139 and the light irradiation portion 239 are arranged so that the position of the light irradiation portion 239 in the direction of the axis O (X-axis direction) is at a substantially center of the light transmitting portion 139 in the direction of the axis O. Therefore, the operator can more easily achieve alignment between the light transmitting portion 139 and the light irradiation portion 239.

Second Embodiment

Figure 6:
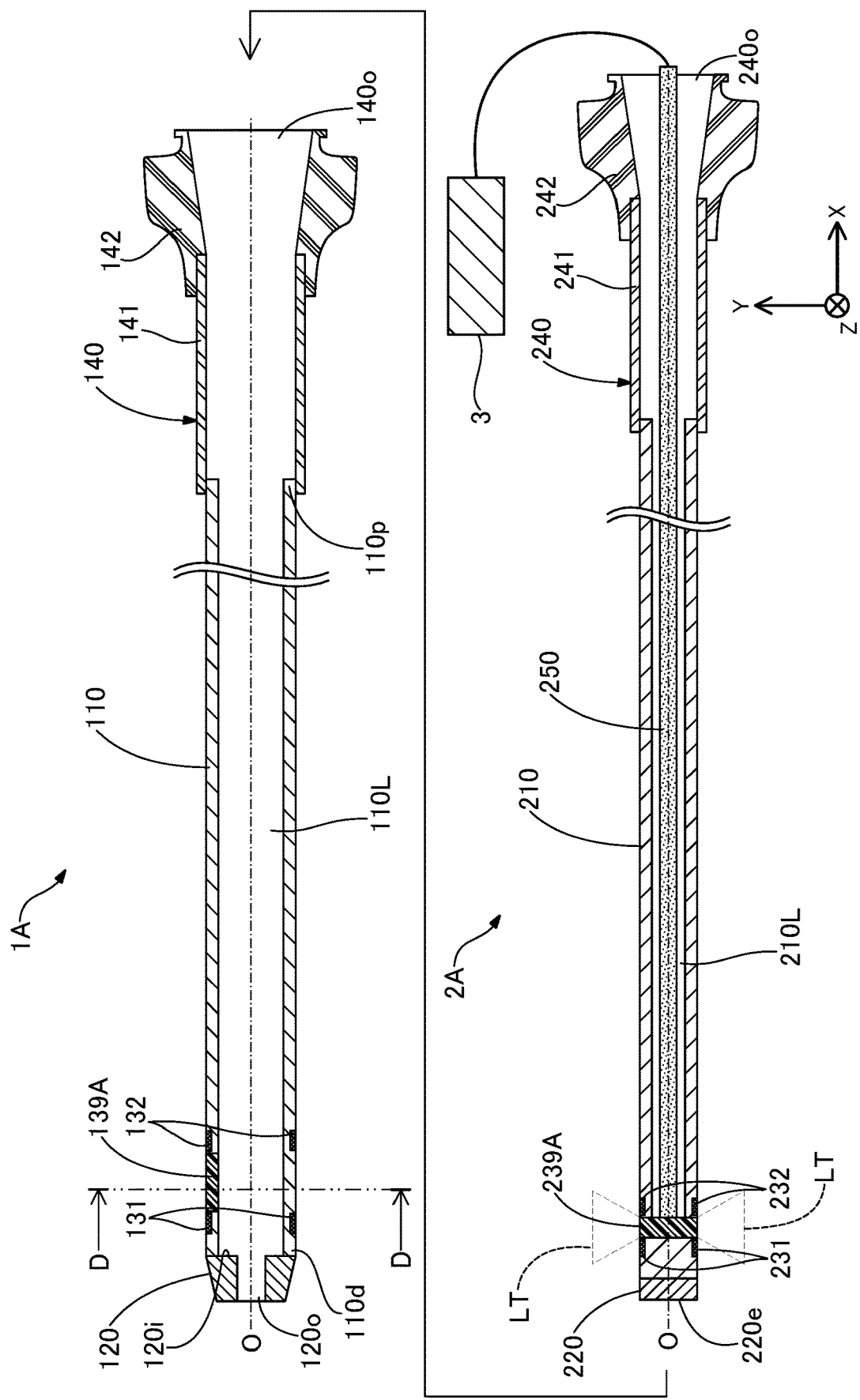
FIG. 6 is an explanatory diagram illustrating a configuration of a light irradiation system of a second embodiment.
Figure 7:
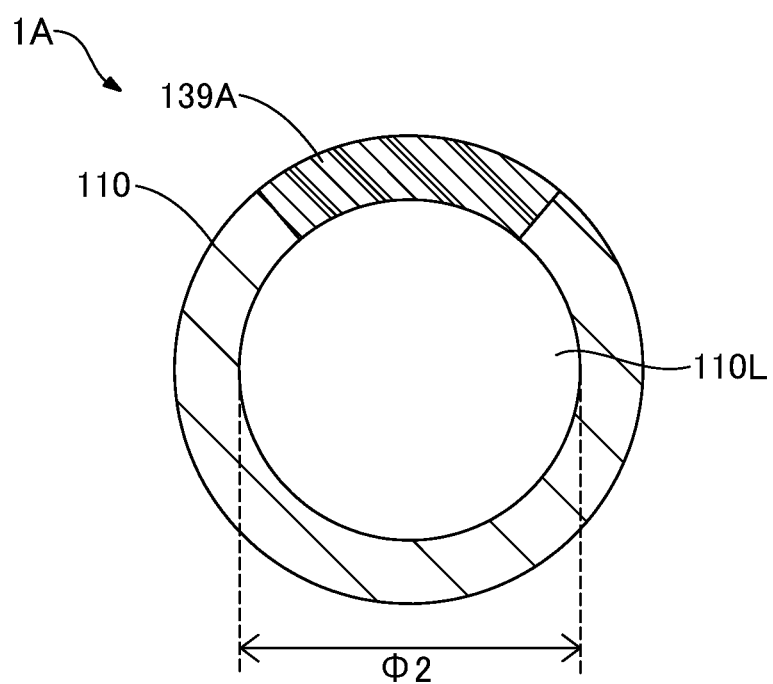
FIG. 7 is an explanatory diagram illustrating a cross-sectional configuration taken along line D-D of FIG. 6.

FIG. 6 is an explanatory diagram illustrating a configuration of a light irradiation system of a second embodiment. FIG. 7 is an explanatory diagram illustrating a cross-sectional configuration taken along line D-D of FIG. 6. The light irradiation system of the second embodiment includes a catheter 1A and a light irradiation device 2A having configurations different from those of the first embodiment. The catheter 1A includes a light transmitting portion 139A instead of the light transmitting portion 139. As illustrated in FIG. 7, the light transmitting portion 139A is a plate-like member having an arc shape, and is fitted into a part of the shaft 110 and joined to the shaft 110. Thus, the light transmitting portion 139A of the second embodiment is provided partially in the circumferential direction, and from the part in the circumferential direction, transmits light inside the shaft 110 to the outside. It is noted that the light transmitting portion 139A can be formed of a similar material as the light transmitting portion 139.

The light irradiation device 2A includes a light irradiation portion 239A, instead of the light irradiation portion 239. As illustrated in FIG. 6, the light irradiation portion 239A is a solid, substantially columnar member having a diameter that is substantially the same as the outer diameter of the shaft 210. The light irradiation portion 239A is joined to the shaft 210 at each of the proximal end side and the distal end side. Further, a surface of the light irradiation portion 239A at the proximal end side covers an exposed distal end of the core of the optical fiber 250. Therefore, in the light irradiation device 2A, the laser light LT generated by the laser light generator 3 is output, for irradiation, to the outside from the entire circumference of the light irradiation device 2A via the light irradiation portion 239A (FIG. 6).

Figure 8:
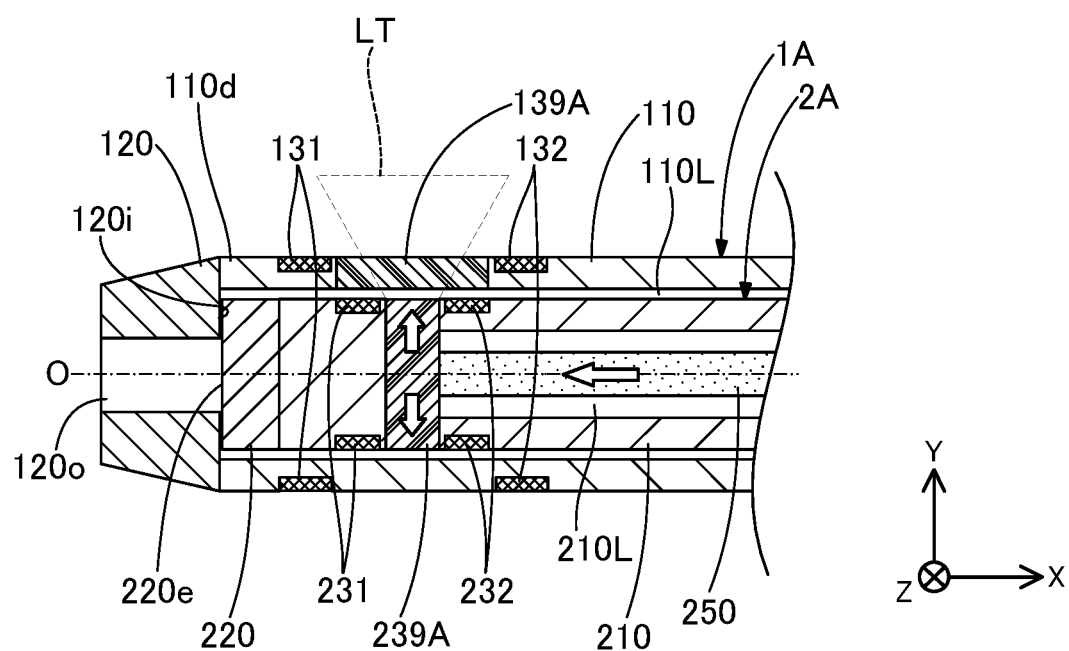
FIG. 8 is an explanatory diagram illustrating a usage state of the light irradiation system of the second embodiment.

FIG. 8 is an explanatory diagram illustrating a usage state of the light irradiation system of the second embodiment. A method of using the light irradiation system of the second embodiment is similar to the one of the first embodiment. In the light irradiation system of the second embodiment, as illustrated in FIG. 8, the light transmitting portion 139A of the catheter 1A is provided partially in the circumferential direction, whereas the light irradiation portion 239A of the light irradiation device 2A is provided wholly in the circumferential direction. Therefore, similarly to the first embodiment, the operator only needs to achieve alignment between the light transmitting portion 139A and the light irradiation portion 239A in the direction of the axis O (X-axis direction), and does not need to achieve alignment between the light transmitting portion 139A and the light irradiation portion 239A in the circumferential direction (YZ-axis direction).

FIG. 9 is an explanatory table showing combinations of the light transmitting portion 139 and the light irradiation portion 239. As shown in FIG. 9, any combination between the light transmitting portion 139 described in the first embodiment and the light transmitting portion 139A described in the second embodiment, and the light irradiation portion 239 described in the first embodiment and the light irradiation portion 239A described in the second embodiment is possible. That is, as shown in No. 1, the light irradiation system may have a configuration in which the light transmitting portion 139 (FIG. 1) that transmits light in the entire circumference and the light irradiation portion 239 (FIG. 1) that outputs irradiation light partially in the circumferential direction are combined. Further, as shown in No. 2, the light irradiation system may have a configuration in which the light transmitting portion 139A (FIG. 6) that transmits light partially in the circumferential direction and the light irradiation portion 239A (FIG. 6) that outputs irradiation light in the entire circumference are combined. Moreover, as shown in No. 3, the light irradiation system may have a configuration in which the light transmitting portion 139 (FIG. 1) that transmits light in the entire circumference and the light irradiation portion 239A (FIG. 6) that outputs irradiation light in the entire circumference are combined. Further, as shown in No. 4, the light irradiation system may have a configuration in which the light transmitting portion 139A (FIG. 6) that transmits light partially in the circumferential direction and the light irradiation portion 239 (FIG. 1) that outputs irradiation light partially in the circumferential direction are combined. According to the light irradiation system of the second embodiment described above, an effect similar to the first embodiment described above can be achieved.

Third Embodiment

Figure 10:
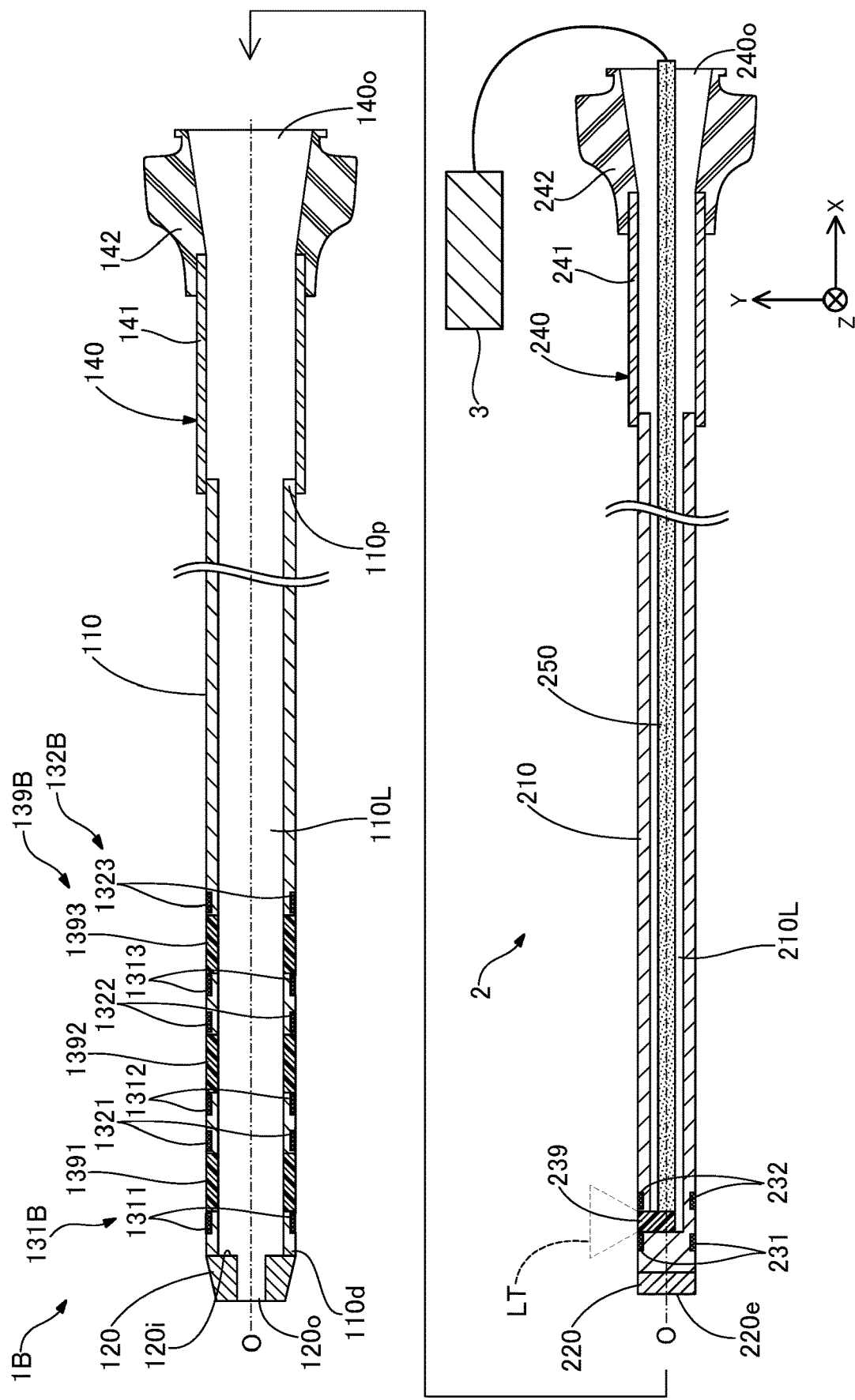
FIG. 10 is an explanatory diagram illustrating a configuration of a light irradiation system of a third embodiment.

FIG. 10 is an explanatory diagram illustrating a configuration of a light irradiation system of a third embodiment. The light irradiation system of the third embodiment includes a catheter 1B having a configuration different from that of the first embodiment, and the light irradiation device 2 having a configuration similar to that of the first embodiment. The catheter 1B includes a light transmitting portion 139B instead of the light transmitting portion 139, and includes first marker portions 131B and 132B instead of the first marker portions 131 and 132. As illustrated in FIG. 10, the light transmitting portion 139B is composed of three light transmitting portions 1391, 1392, and 1393 arranged side by side in the direction of the axis O (X-axis direction). The configurations of the light transmitting portions 1391, 1392, and 1393 are similar to that of the light transmitting portion 139 described in the first embodiment.

Further, the first marker portions 131B and 132B are composed of first marker portions 1311 and 1321 that function as marks indicating a position of the light transmitting portion 1391, first marker portions 1312 and 1322 that function as marks indicating a position of the light transmitting portion 1392, and first marker portions 1313 and 1323 that function as marks indicating a position of the light transmitting portion 1393. The first marker portion 1311 is provided close to the distal end portion of the light transmitting portion 1391, and the first marker portion 1321 is provided close to the proximal end portion of the light transmitting portion 1391. The first marker portion 1312 is provided close to the distal end portion of the light transmitting portion 1392, and the first marker portion 1322 is provided close to the proximal end portion of the light transmitting portion 1392. The first marker portion 1313 is provided close to the distal end portion of the light transmitting portion 1393, and the first marker portion 1323 is provided close to the proximal end portion of the light transmitting portion 1393. The configurations of the first marker portions 1311 to 1323 are similar to those of the first marker portions 131 and 132 described in the first embodiment. It is noted that first marker portions adjacent to each other in the direction of the axis O, specifically, the first marker portions 1321 and 1312 and the first marker portions 1322 and 1313 may be formed as one connected marker portion.

Thus, the catheter 1B may be provided with a plurality of sets of the light transmitting portions 1391 to 1393 and the first marker portions 1311 to 1323. In the example of FIG. 10, a case in which three sets of the light transmitting portions 1391 to 1393 and the first marker portions 1311 to 1323 are provided is described, but two sets or four or more sets may be provided. According to the light irradiation system of the third embodiment described above, an effect similar to the first embodiment described above can be achieved. Further, in the light irradiation system of the third embodiment, a plurality of sets of the light transmitting portions 1391 to 1393 and the first marker portions 1311 to 1323 are provided, and thus, different regions of the catheter 1B in the direction of the axis O can be irradiated with light by moving only the light irradiation device 2 in the direction of the axis O (X-axis direction) inside the catheter 1B, without moving the catheter 1B in the living body lumen. Moreover, the first marker portions 1311 to 1323 are provided for the plurality of light transmitting portions 1391 to 1393, respectively, and thus, it is possible to easily align the light irradiation portion 239 with each of the light transmitting portions 1391 to 1393.

Fourth Embodiment

Figure 11:
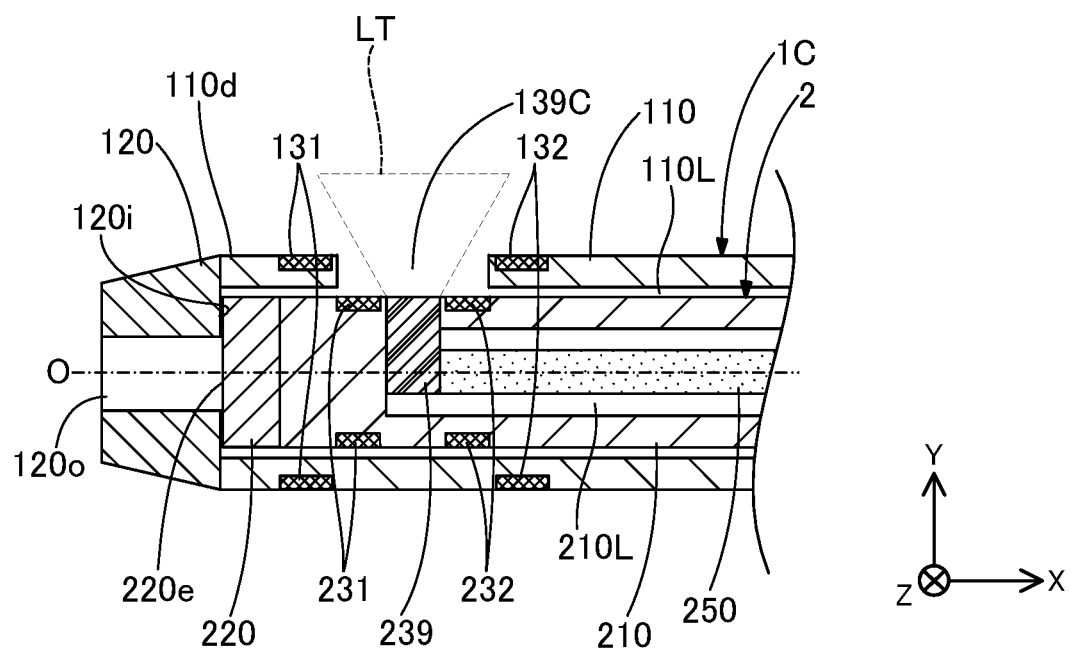
FIG. 11 is an explanatory diagram illustrating a configuration of a light irradiation system of a fourth embodiment.

FIG. 11 is an explanatory diagram illustrating a configuration of a light irradiation system of a fourth embodiment. The light irradiation system of the fourth embodiment includes a catheter 1C having a configuration different from that of the first embodiment, and the light irradiation device 2 having a configuration similar to that of the first embodiment. FIG. 11 illustrates a state where the light irradiation device 2 is inserted into the catheter 1C. The catheter 1C includes a light transmitting portion 139C instead of the light transmitting portion 139. The light transmitting portion 139C is a through-hole formed partially in a circumference of the shaft 110, and the inside of the shaft 110 is in communication with the outside of the shaft 110 via the light transmitting portion 139C. In the light transmitting portion 139C of the fourth embodiment, the light inside the shaft 110 can be transmitted to the outside via this through-hole. Thus, various configurations can be adopted for the light transmitting portion 139C, and the light transmitting portion 139C may be formed without using a separate member. According to the light irradiation system of the fourth embodiment described above, an effect similar to the first embodiment described above can be achieved. Further, in the light irradiation system of the fourth embodiment, the light transmitting portion 139C can be easily formed, and the manufacturing cost of the catheter 1C can be reduced, compared with a case where a separate member is used.

Fifth Embodiment

Figure 12:
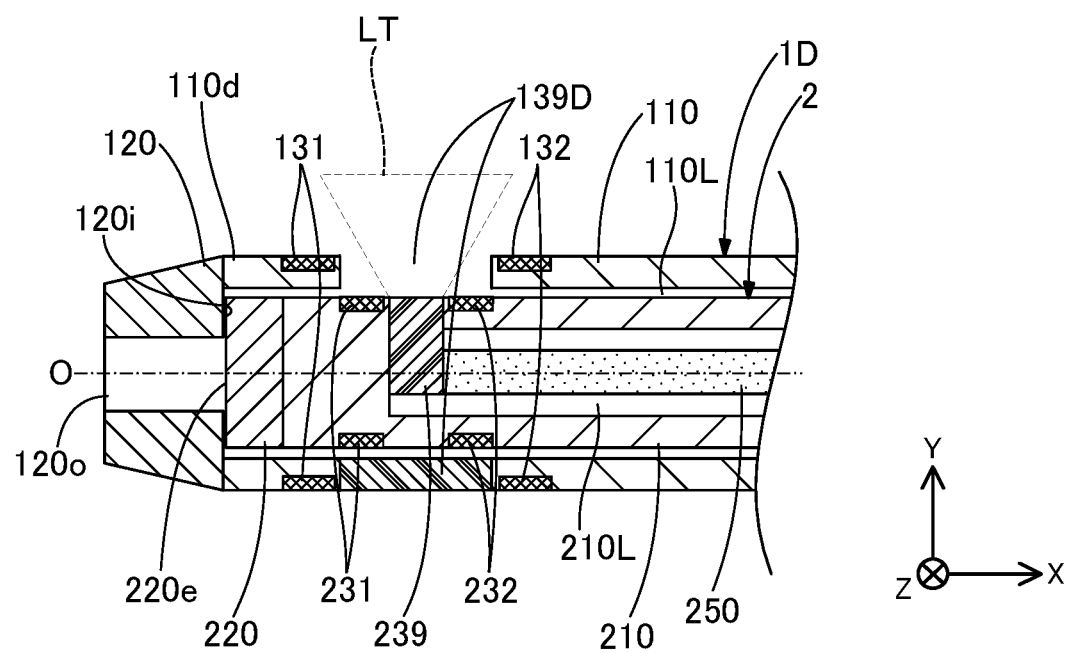
FIG. 12 is an explanatory diagram illustrating a configuration of a light irradiation system of a fifth embodiment.

FIG. 12 is an explanatory diagram illustrating a configuration of a light irradiation system of a fifth embodiment. The light irradiation system of the fifth embodiment includes a catheter 1D having a configuration different from that of the first embodiment, and the light irradiation device 2 having a configuration similar to that of the first embodiment. FIG. 12 illustrates a state where the light irradiation device 2 is inserted into the catheter 1D. The catheter 1D includes a light transmitting portion 139D instead of the light transmitting portion 139. The light transmitting portion 139D includes a part for allowing light to be transmitted via a through-hole (FIG. 12: +Y-axis direction) and a part for allowing light to be transmitted by a plate-like member having an arc shape (FIG. 12: −Y-axis direction). The through-hole and the plate-like member are each provided at least partially in the circumferential direction. For example, an upper half of the light transmitting portion 139D with respect to the axis O may be the through-hole, and a lower half of the light transmitting portion 139D with respect to the axis O may be the plate-like member. Thus, various configurations can be adopted for the light transmitting portion 139D, and the light transmitting portion 139D may be formed using a combination of a plurality of light transmitting means. According to the light irradiation system of the fifth embodiment described above, an effect similar to the first embodiment described above can be achieved. Further, in the light irradiation system of the fifth embodiment, setting different light transmittances for the plurality of light transmitting means makes it possible to adjust the intensity of irradiation light output to the outside, for example.

Sixth Embodiment

Figure 13:
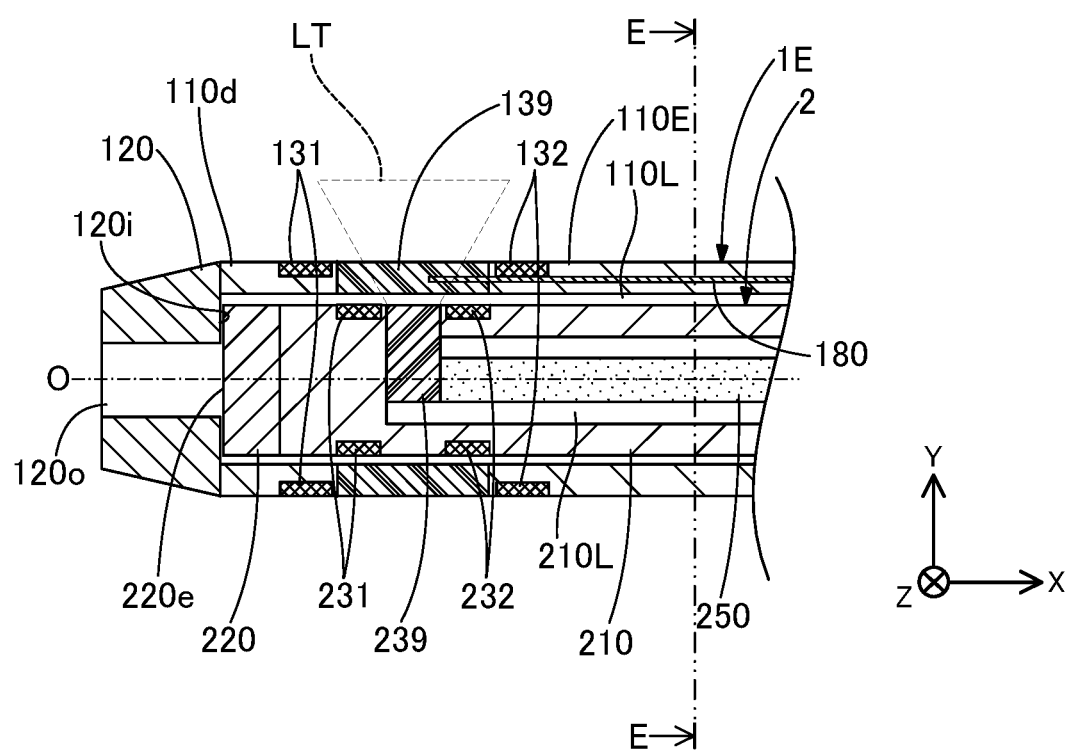
FIG. 13 is an explanatory diagram illustrating a configuration of a light irradiation system of a sixth embodiment.
Figure 14:
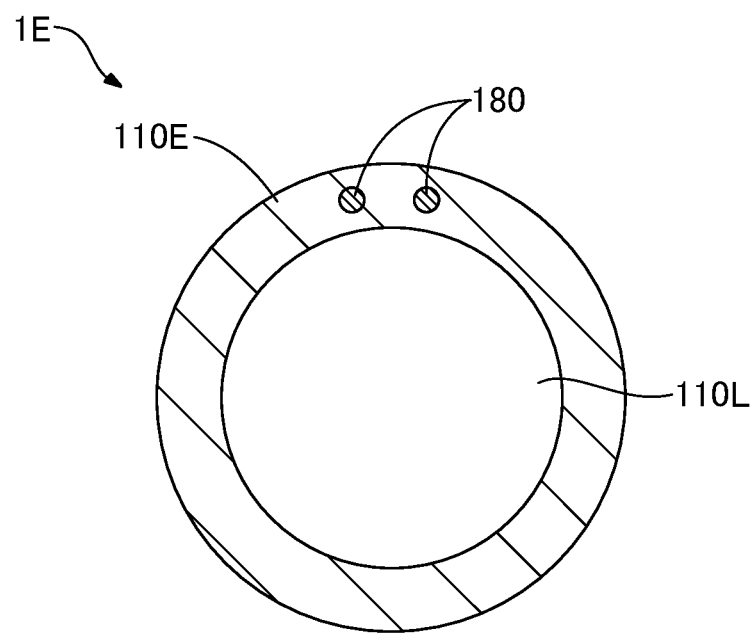
FIG. 14 is an explanatory diagram illustrating a cross-sectional configuration taken along line E-E of FIG. 13.

FIG. 13 is an explanatory diagram illustrating a configuration of a light irradiation system of a sixth embodiment. FIG. 14 is an explanatory diagram illustrating a cross-sectional configuration taken along line E-E of FIG. 13. The light irradiation system of the sixth embodiment includes a catheter 1E having a configuration different from that of the first embodiment, and the light irradiation device 2 having a configuration similar to that of the first embodiment. FIG. 13 illustrates a state where the light irradiation device 2 is inserted into the catheter 1E. In addition to the elements of the configuration described in the first embodiment, the catheter 1E further includes a temperature sensor 180. As illustrated in FIG. 14, the temperature sensor 180 includes two different types of metal conductors and measures the temperature in the vicinity of the light transmitting portion 139. The temperature sensor 180 is embedded in the light transmitting portion 139 and the shaft 110. A distal end side of the temperature sensor 180 is arranged inside the light transmitting portion 139, and a proximal end side of the temperature sensor 180 is connected to a not-illustrated thermometer. It is noted that at least a part of the distal end side of the temperature sensor 180 may protrude from an outer surface of the light transmitting portion 139 or the shaft 110. The temperature sensor 180 may be provided in at least one of the catheter 1E and the light irradiation device 2, or may be provided in both of the catheter 1E and the light irradiation device 2.

Thus, the catheter 1E and the light irradiation device 2 can be provided with various elements not described in the configuration above. According to the light irradiation system of the sixth embodiment described above, an effect similar to the first embodiment described above can be achieved. Further, the light irradiation system of the sixth embodiment includes the temperature sensor 180 that measures the temperature at least in the vicinity of the light transmitting portion 139, and thus, it is possible to observe in real time a temperature change in living tissue due to the light irradiation, which can contribute to the suppression of blood coagulation and damage of living tissue due to the light irradiation.

Seventh Embodiment

Figure 15:
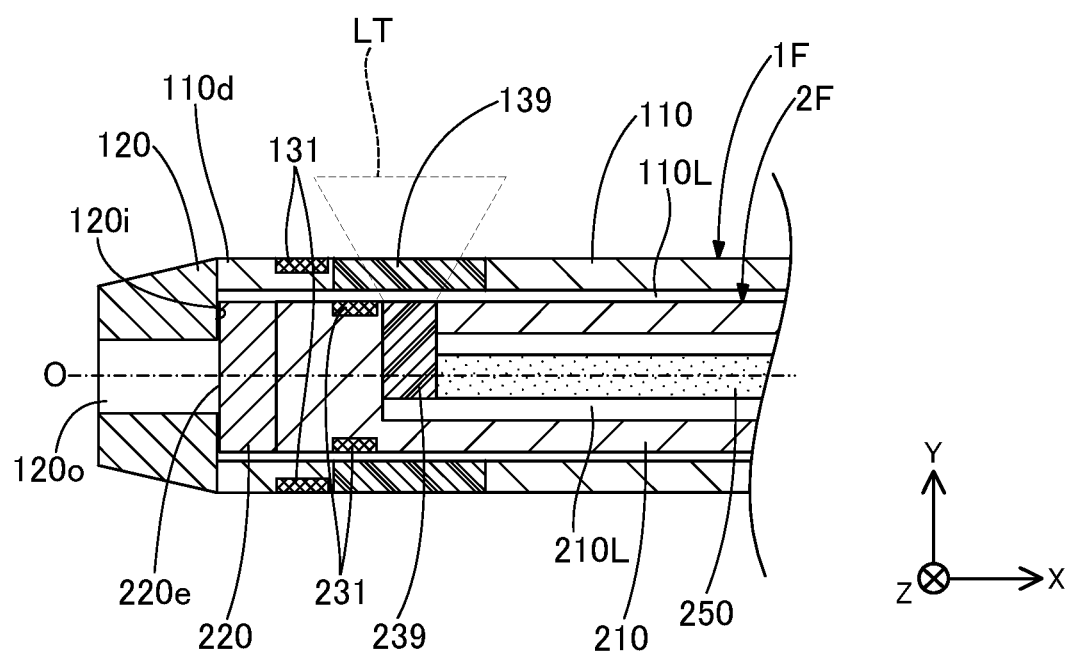
FIG. 15 is an explanatory diagram illustrating a configuration of a light irradiation system of a seventh embodiment.

FIG. 15 is an explanatory diagram illustrating a configuration of a light irradiation system of a seventh embodiment. The light irradiation system of the seventh embodiment includes a catheter 1F and a light irradiation device 2F having configurations different from those of the first embodiment. FIG. 15 illustrates a state where the light irradiation device 2F is inserted into the catheter 1F. The catheter 1F does not include the first marker portion 132 described in the first embodiment. Similarly, the light irradiation device 2F does not include the second marker portion 232 described in the first embodiment. Thus, various configurations can be adopted for the first marker portion and the second marker portion. For example, instead of omitting the first and second marker portions 132 and 232, the first and second marker portions 131 and 231 may be omitted. According to the light irradiation system of the seventh embodiment described above, an effect similar to the first embodiment described above can be achieved. Further, in the light irradiation system of the seventh embodiment, the manufacturing cost of the catheter 1F and the light irradiation device 2F can be reduced, compared with a configuration in which marker portions are provided at both ends of the light transmitting portion 139 and the light irradiation portion 239.

Eighth Embodiment

Figure 16:
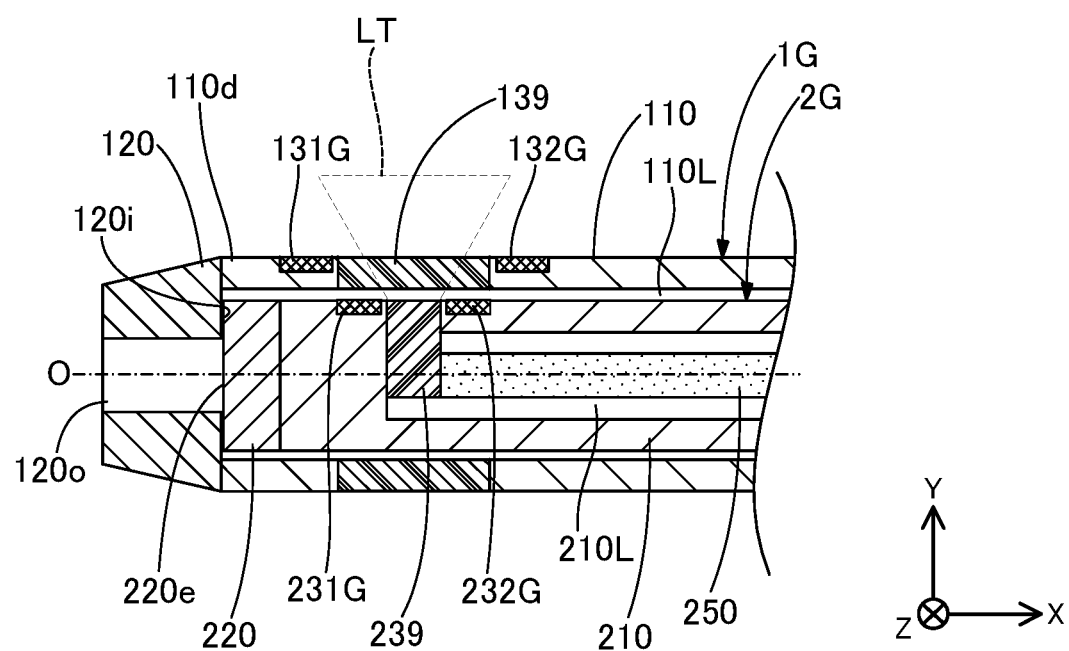
FIG. 16 is an explanatory diagram illustrating a configuration of a light irradiation system of an eighth embodiment.

FIG. 16 is an explanatory diagram illustrating a configuration of a light irradiation system of an eighth embodiment. The light irradiation system of the eighth embodiment includes a catheter 1G and a light irradiation device 2G having configurations different from those of the first embodiment. FIG. 16 illustrates a state where the light irradiation device 2G is inserted into the catheter 1G. The catheter 1G includes first marker portions 131G and 132G, instead of the first marker portions 131 and 132 described in the first embodiment. The light irradiation device 2G includes second marker portions 231G and 232G instead of the second marker portions 231 and 232 described in the first embodiment.

FIG. 17 is an explanatory diagram illustrating a configuration of the catheter 1G of the eighth embodiment. FIG. 17(A) illustrates an example of a configuration of the catheter 1G viewed from the +Y-axis direction, and FIG. 17(B) illustrates another example of the configuration of the catheter 1G viewed from the +Y-axis direction. The first marker portions 131G and 132G are each provided partially in the circumference of the catheter 1G. In the example of FIG. 17(A), the first marker portion 131G is provided along one side of the light transmitting portion 139 on the distal end side, in substantially the same range as the light transmitting portion 139. Similarly, the first marker portion 132G is provided along one side of the light transmitting portion 139 on the proximal end side, in substantially the same range as the light transmitting portion 139. In the example of FIG. 17(B), the first marker portions 131G and 132G are provided along the periphery of the light transmitting portion 139 to surround the light transmitting portion 139. Similarly, the second marker portions 231G and 232G are provided along one side of the light irradiation portion 239, or surround the periphery of the light irradiation portion 239.

Thus, various configurations can be adopted for the first marker portion and the second marker portion, and as illustrated in the drawings, the first marker portion and the second marker portion may be provided only partially in the circumferential direction. According to the light irradiation system of the eighth embodiment described above, an effect similar to the first embodiment described above can be achieved. Further, in the light irradiation system of the eighth embodiment, the manufacturing cost of the catheter 1G and the light irradiation device 2G can be reduced, compared with a configuration in which a marker portion is provided wholly in the circumferential direction.

Ninth Embodiment

Figure 18:
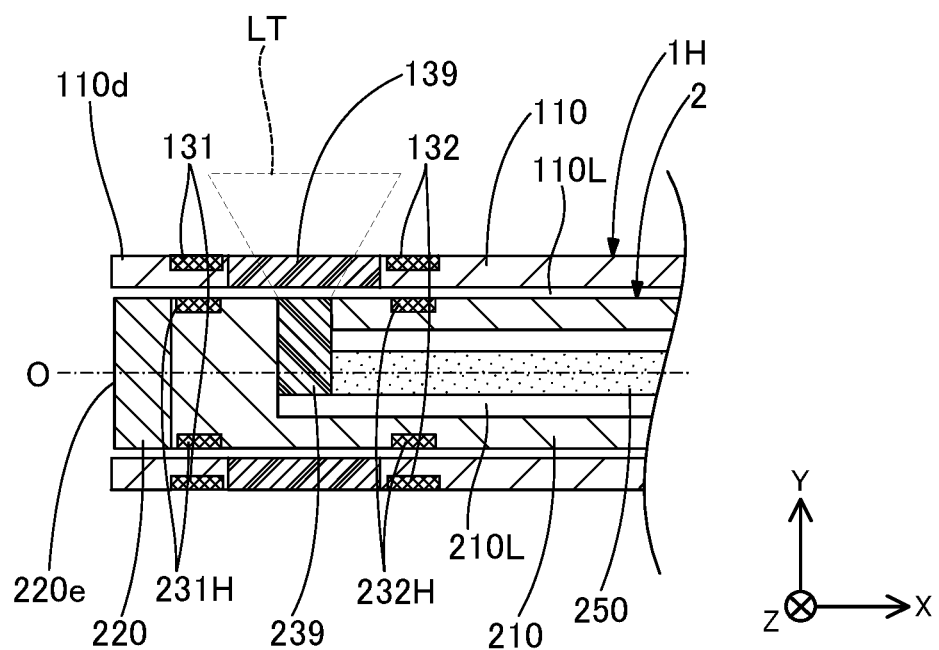
FIG. 18 is an explanatory diagram illustrating a configuration of a light irradiation system of a ninth embodiment.

FIG. 18 is an explanatory diagram illustrating a configuration of a light irradiation system of a ninth embodiment. The light irradiation system of the ninth embodiment includes a catheter 111 having a configuration different from that of the first embodiment, and the light irradiation device 2 having a configuration similar to that of the first embodiment. FIG. 18 illustrates a state where the light irradiation device 2 is inserted into the catheter 111. The catheter 111 does not include the distal tip 120 described in the first embodiment. It is noted that, similarly, the distal tip 220 of the light irradiation device 2 may be omitted. Thus, various configurations can be adopted for the catheter 111 and the light irradiation device 2, and some of the above-mentioned constituent components may be omitted. In the light irradiation system of the ninth embodiment, alignment between the light transmitting portion 139 and the light irradiation portion 239 can also be achieved by using the first marker portions 131 and 132 provided at both ends of the light transmitting portion 139 and the second marker portions 231 and 232 provided at both ends of the light irradiation portion 239, and thus, an effect similar to the first embodiment can be achieved. Further, in the light irradiation system of the ninth embodiment, the manufacturing cost of the catheter 111 can be reduced, compared with a configuration in which the distal tip 120 is provided.

Tenth Embodiment

Figure 19:
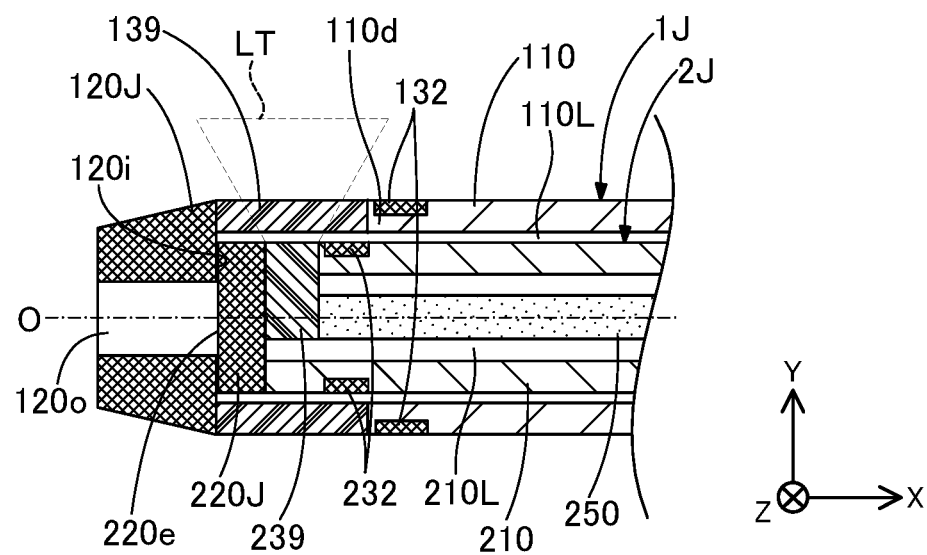
FIG. 19 is an explanatory diagram illustrating a configuration of a light irradiation system of a tenth embodiment.

FIG. 19 is an explanatory diagram illustrating a configuration of a light irradiation system of a tenth embodiment. The light irradiation system of the tenth embodiment includes a catheter 1J and a light irradiation device 2J having configurations different from those of the first embodiment. FIG. 19 illustrates a state where the light irradiation device 2J is inserted into the catheter 1J. The catheter 1J includes a distal tip 120J instead of the distal tip 120 described in the first embodiment. The light irradiation device 2J includes a distal tip 220J instead of the distal tip 220 described in the first embodiment. The distal tip 120J is provided close to the distal end portion of the light transmitting portion 139, and functions as a mark indicating a position of the distal end portion of the light transmitting portion 139. Similarly, the distal tip 220J is provided close to the distal end portion of the light irradiation portion 239, and functions as a mark indicating a position of the distal end portion of the light irradiation portion 239. FIG. 19 illustrates an example in which the distal tip 120J and the light transmitting portion 139 are adjacent to each other and the distal tip 220J and the light irradiation portion 239 are adjacent to each other, but the shaft 110 and the shaft 210 may be interposed between the distal tip 120J and the light transmitting portion 139, and the distal tip 220J and the light irradiation portion 239. The distal tip 120J and the distal tip 220J can be formed of a radiopaque resin material or a radiopaque metal material, similarly to the first marker portion 131 and the like described in the first embodiment.

Thus, the distal tip 120J may function as the first marker portion 131, and the distal tip 220J may function as the second marker portion 231. According to the light irradiation system of the tenth embodiment described above, an effect similar to the first embodiment described above can be achieved. Further, in the light irradiation system of the tenth embodiment, the manufacturing cost of the catheter 1J and the light irradiation device 2J can be reduced, compared with a configuration in which the first marker portion 131 and the second marker portion 231 are provided.

Eleventh Embodiment

Figure 20:
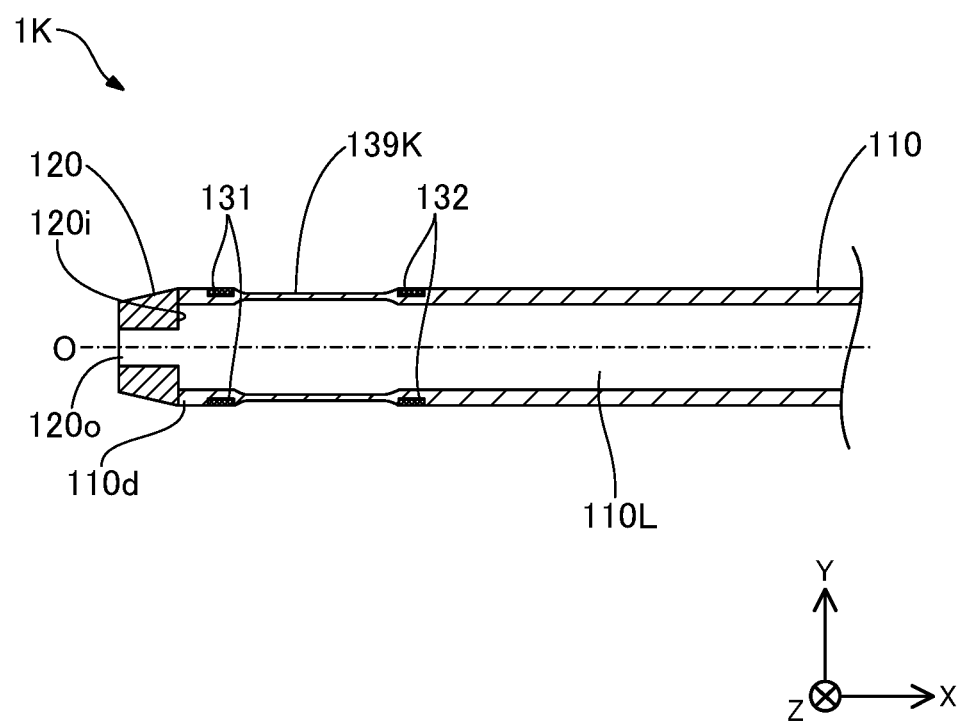
FIG. 20 is an explanatory diagram illustrating a configuration of a light transmission device of an eleventh embodiment.

FIG. 20 is an explanatory diagram illustrating a configuration of a light transmission device 1K of an eleventh embodiment. A catheter 1K illustrated in FIG. 20 includes a light transmitting portion 139K instead of the light transmitting portion 139 of the first embodiment. The light transmitting portion 139K is formed by thinning a part of the shaft 110. A wall thickness (a thickness in the YZ-axis direction) of the light transmitting portion 139K is thinner than that of the shaft 110, and thus, emission light from the light irradiation device 2 (FIG. 1 and the like) can be transmitted by the light transmitting portion 139K. Therefore, the light transmitting portion 139K may be formed without using a separate member.

Figure 21:
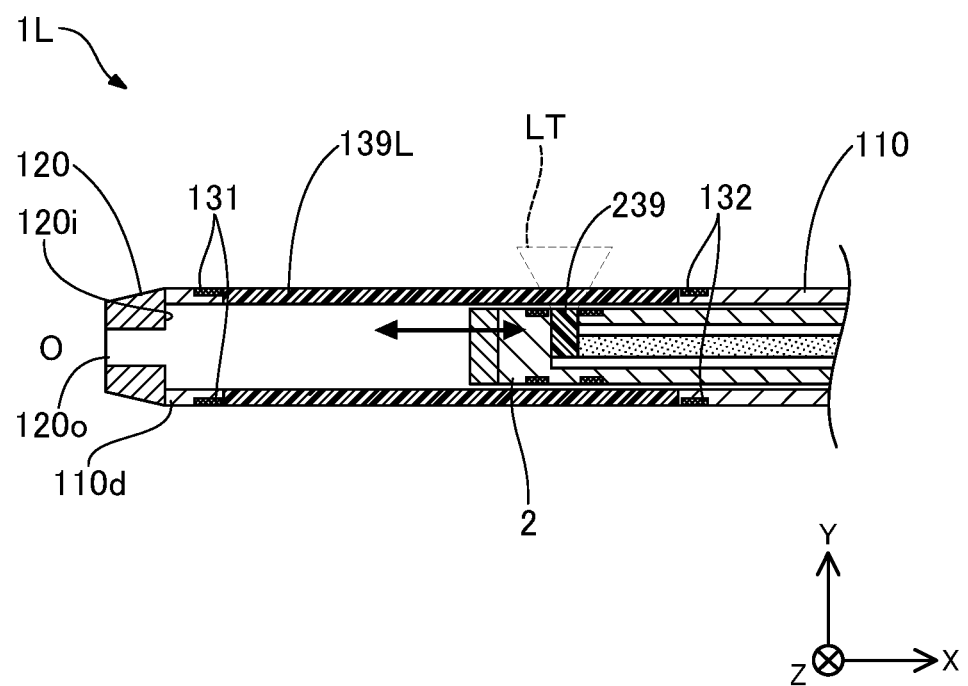
FIG. 21 is an explanatory diagram illustrating a configuration of a catheter of the eleventh embodiment.

FIG. 21 is an explanatory diagram illustrating a configuration of a catheter 1L of the eleventh embodiment. The catheter 1L illustrated in FIG. 21 includes a light transmitting portion 139L instead of the light transmitting portion 139 of the first embodiment. A length of the light transmitting portion 139L in the direction of the axis O (X-axis direction) is longer than that of the light transmitting portion 139 described in the first embodiment. When the light transmitting portion 139L is employed, the light irradiation device 2 can be moved in the direction of the axis O, toward any position within a range where the light transmitting portion 139L is formed, for irradiating a target location with the emission light LT. Further, irradiation with the emission light LT can be performed over a wide range by moving only the light irradiation device 2, without moving the catheter 1L.

Figure 22:
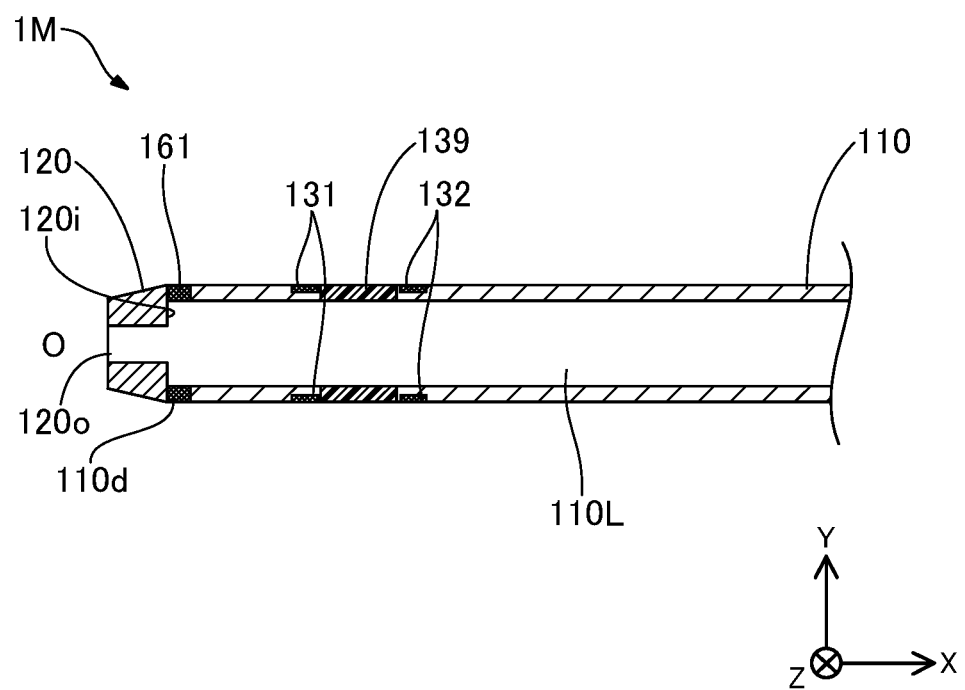
FIG. 22 is an explanatory diagram illustrating a configuration of the catheter of the eleventh embodiment.

FIG. 22 is an explanatory diagram illustrating a configuration of a catheter 1M of the eleventh embodiment. In addition to the elements of the configuration described in the first embodiment, the catheter 1M illustrated in FIG. 22 further includes a marker 161. The marker 161 is distal to the first marker portion 131 and functions as a mark indicating a distal end of the catheter 1M. The marker 161 allows the operator to advance the catheter 1M in the living body lumen, while observing positions of the marker 161 and the first marker portion 131. Further, if the marker 161 is provided, it is possible to suppress a displacement of the catheter 1M when the light irradiation device 2 is inserted. It is noted that the marker 161 and the first marker portion 131 illustrated in the drawing may be integrally formed.

Thus, various modifications can be applied to the catheter 1K, and it is possible to apply any modification with respect to a method of forming light transmitting portions 139K to 139M, a range in the direction of the axis O (X-axis direction) in which the light transmitting portions 139K to 139M are provided, and a range in the circumferential direction in which the light transmitting portions 139K to 139M are provided. According to the light irradiation systems using the catheters 1K to 1M of the eleventh embodiment described above, an effect similar to the first embodiment described above can be achieved.

Twelfth Embodiment

Figure 23:
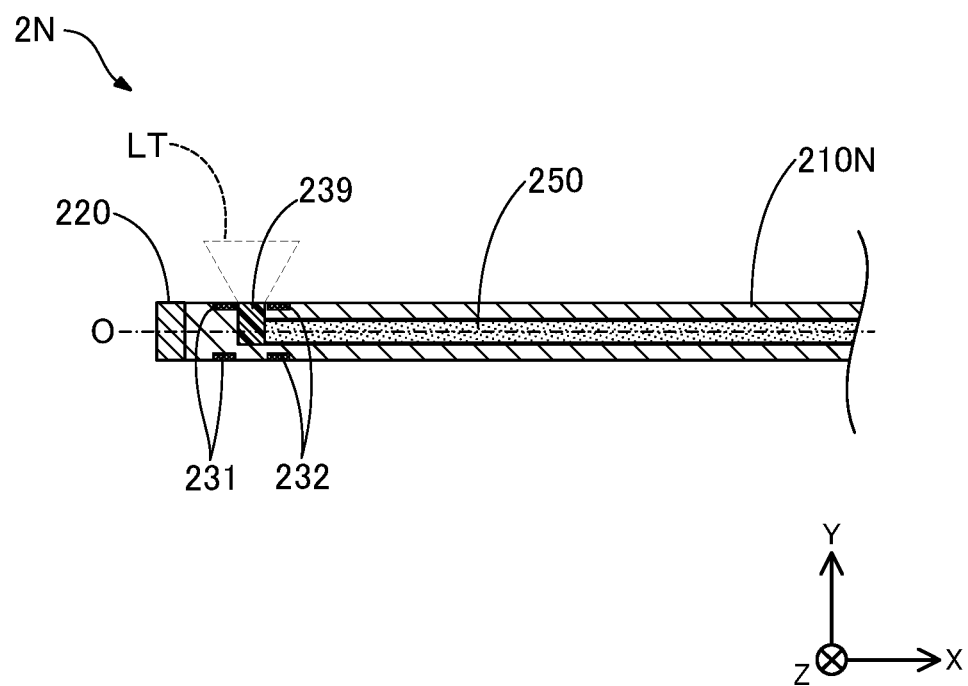
FIG. 23 is an explanatory diagram illustrating a configuration of a light irradiation device of a twelfth embodiment.

FIG. 23 is an explanatory diagram illustrating a configuration of a light irradiation device 2N of a twelfth embodiment. The light irradiation device 2N illustrated in FIG. 23 includes a shaft 210N instead of the shaft 210 of the first embodiment. The shaft 210N surrounds an outer surface of the optical fiber 250 in a state where the shaft 210N contacts the outer surface of the optical fiber 250, and the lumen 210L is not provided inside the shaft 210N. According to the shaft 210N described above, the diameter of the light irradiation device 2N can be further reduced.

Figure 24:
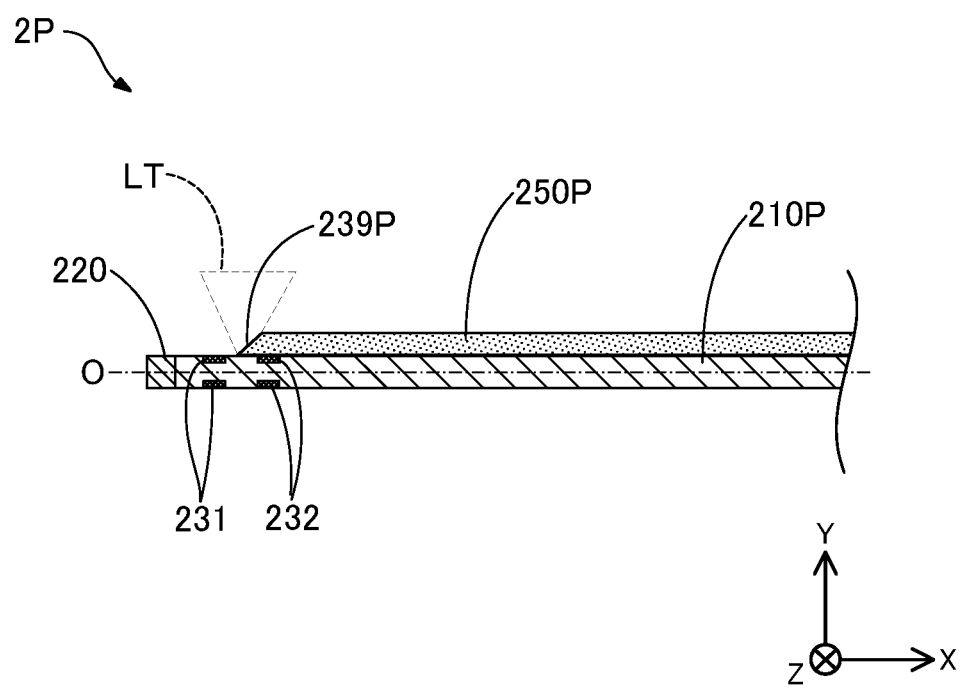
FIG. 24 is an explanatory diagram illustrating a configuration of the light irradiation device of the twelfth embodiment.

FIG. 24 is an explanatory diagram illustrating a configuration of a light irradiation device 2P of the twelfth embodiment. The light irradiation device 2P illustrated in FIG. 24 includes a shaft 210P, an optical fiber 250P, and a light irradiation portion 239P instead of the shaft 210, the optical fiber 250, and the light irradiation portion 239 of the first embodiment. The shaft 210P is an elongated columnar member extending along the axis O and does not include a lumen on the inside. The optical fiber 250P is joined to an outer surface of the shaft 210P. A distal end surface of the optical fiber 250P is cut diagonally, and this distal end surface forms the light irradiation portion 239P. Thus, a configuration may be adopted in which the light irradiation portion 239P is not covered by the shaft 210P and is arranged on the surface of the shaft 210P.

Figure 25:
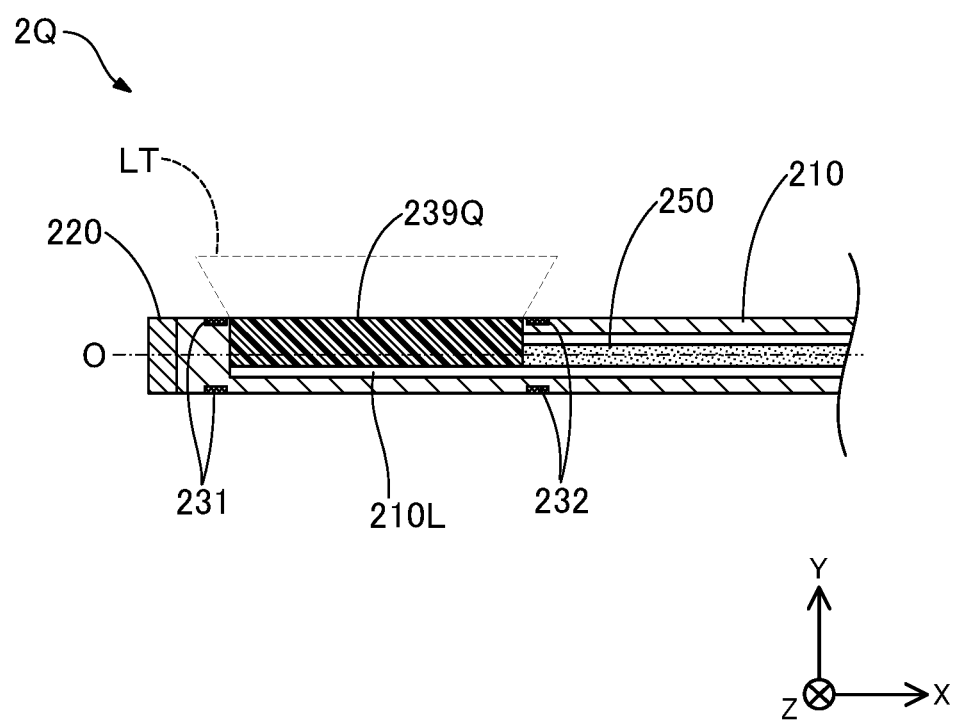
FIG. 25 is an explanatory diagram illustrating a configuration of the light irradiation device of the twelfth embodiment.

FIG. 25 is an explanatory diagram illustrating a configuration of a light irradiation device 2Q of the twelfth embodiment. The light irradiation device 2Q illustrated in FIG. 25 includes a light irradiation portion 239Q instead of the light irradiation portion 239 of the first embodiment. A length of the light irradiation portion 239Q in the direction of the axis O (X-axis direction) is longer than that of the light irradiation portion 239 described in the first embodiment. Therefore, the light irradiation portion 239Q can at once output, for irradiation, the emission light LT to a wider range than the light irradiation portion 239. Employing the light irradiation portion 239Q makes it possible to facilitate an operation of the light irradiation device 2Q. Further, if the light irradiation device 2Q illustrated in FIG. 25 is used in combination with the catheter 1B illustrated in FIG. 10 (a configuration in which a plurality of the light transmitting portions 139B are provided) or the catheter 1L illustrated in FIG. 21 (a configuration in which the light transmitting portion 139L is provided in a wide range), for example, irradiation with the emission light LT to a wide range can easily be performed.

Figure 26:
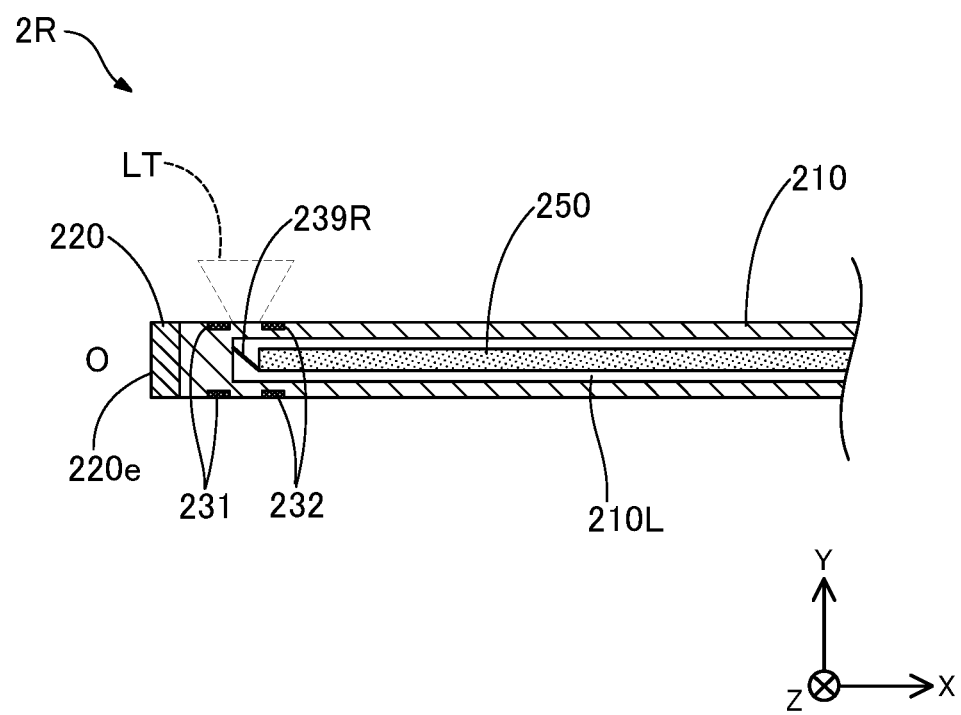
FIG. 26 is an explanatory diagram illustrating a configuration of the light irradiation device of the twelfth embodiment.

FIG. 26 is an explanatory diagram illustrating a configuration of a light irradiation device 2R of the twelfth embodiment. The light irradiation device 2R illustrated in FIG. 26 includes a light irradiation portion 239R instead of the light irradiation portion 239 of the first embodiment. The light irradiation portion 239R is a light-reflecting mirror installed at an angle with respect to a cutting plane of the optical fiber 250 (a cutting plane provided perpendicular to the direction of the axis O). The light irradiation portion 239R reflects the emission light LT from the core of the optical fiber 250 to guide the emission light LT to a side surface of the light irradiation device 2R. Thus, a configuration other than a resin body may be employed for the light irradiation portion 239R. For example, the light irradiation portion 239R may be configured by diagonally cutting a distal end surface of an optical fiber 250R (FIG. 24) without using a light-reflecting mirror.

Thus, various modifications can be applied to the light irradiation devices 2N to 2R, and it is possible to apply any modification with respect to a method of forming light irradiation portions 239N to 239R, a range in the direction of the axis O (X-axis direction) in which the light irradiation portions 239N to 239R are provided, and a range in the circumferential direction in which the light irradiation portions 239N to 239R are provided. According to the light irradiation systems using the light irradiation devices 2N to 2R of the eleventh embodiment described above, an effect similar to the first embodiment described above can be achieved.

Thirteenth Embodiment

Figure 27:
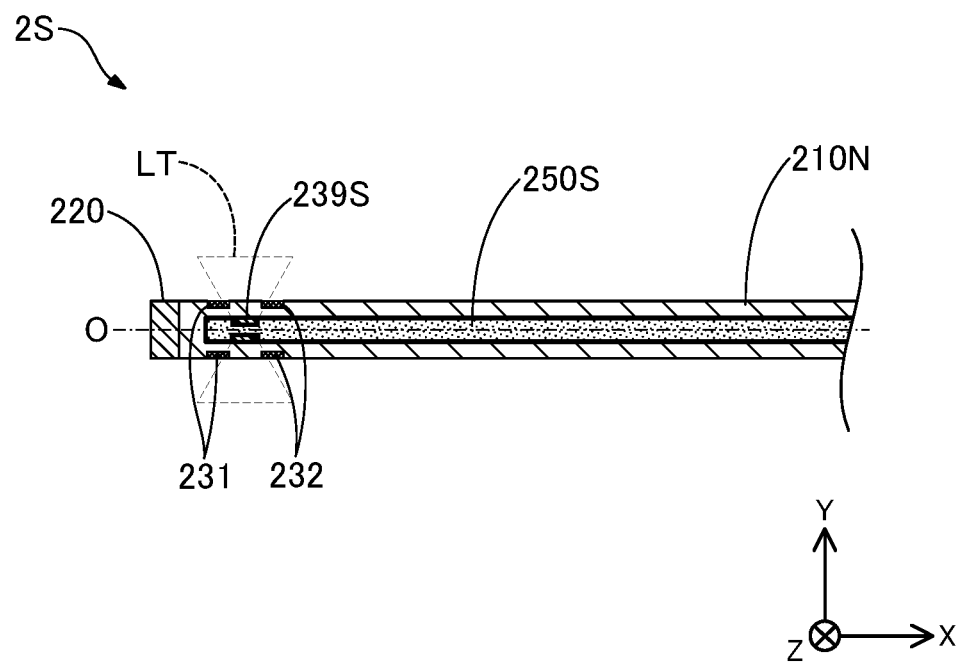
FIG. 27 is an explanatory diagram illustrating a configuration of a light irradiation device of a thirteenth embodiment.
Figure 28:
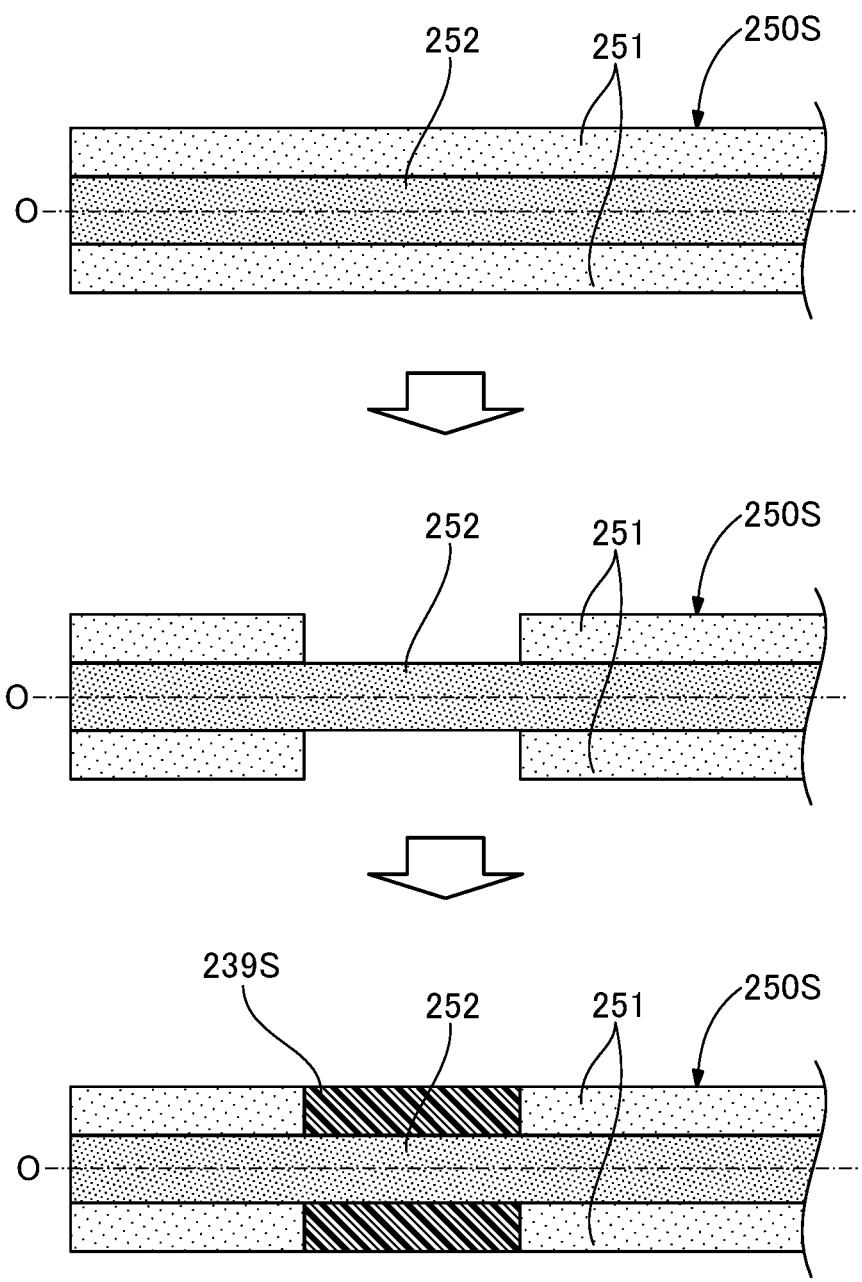
FIG. 28 is an explanatory diagram illustrating a method of forming a light irradiation portion.

FIG. 27 is an explanatory diagram illustrating a configuration of a light irradiation device 2S of a thirteenth embodiment. FIG. 28 is an explanatory diagram illustrating a method of forming a light irradiation portion 239S. The light irradiation device 2S illustrated in FIG. 27 includes the light irradiation portion 239S instead of the light irradiation portion 239 of the twelfth embodiment (FIG. 23), an optical fiber 250S instead of the optical fiber 250, and a shaft 210S instead of the shaft 210N. As illustrated in the lower part of FIG. 28, the light irradiation portion 239S is a light transmitting body that, instead of a clad 251, covers a core 252 in a side surface of a part of the optical fiber 250S on the distal end side. At least a part of the shaft 210S that covers the light irradiation portion 239S, or the entire shaft 210S is formed of a light-transmitting resin material. Therefore, as illustrated in FIG. 27, the emission light LT from the light irradiation portion 239S passes through the shaft 210S and is output, for irradiation, to the outside.

A method of forming the light irradiation portion 239S will be described with reference to FIG. 28. First, the clad 251 is removed from the side surface of a part of the optical fiber 250S on the distal end side. In the example of FIG. 28, the clad 251 is removed over the entire circumference of the optical fiber 250S. It is noted that a range in the direction of the axis O in which the clad 251 is removed may be any range determined in accordance with a length in the direction of the axis O in which the light irradiation portion 239S is to be provided. Next, the part of the optical fiber 250S from which the clad 251 is removed is filled with a light-transmitting material (a resin or a metal). As a result, as illustrated in FIG. 28, the light irradiation portion 239S is formed over the entire circumference of the optical fiber 250S.

Figure 29:
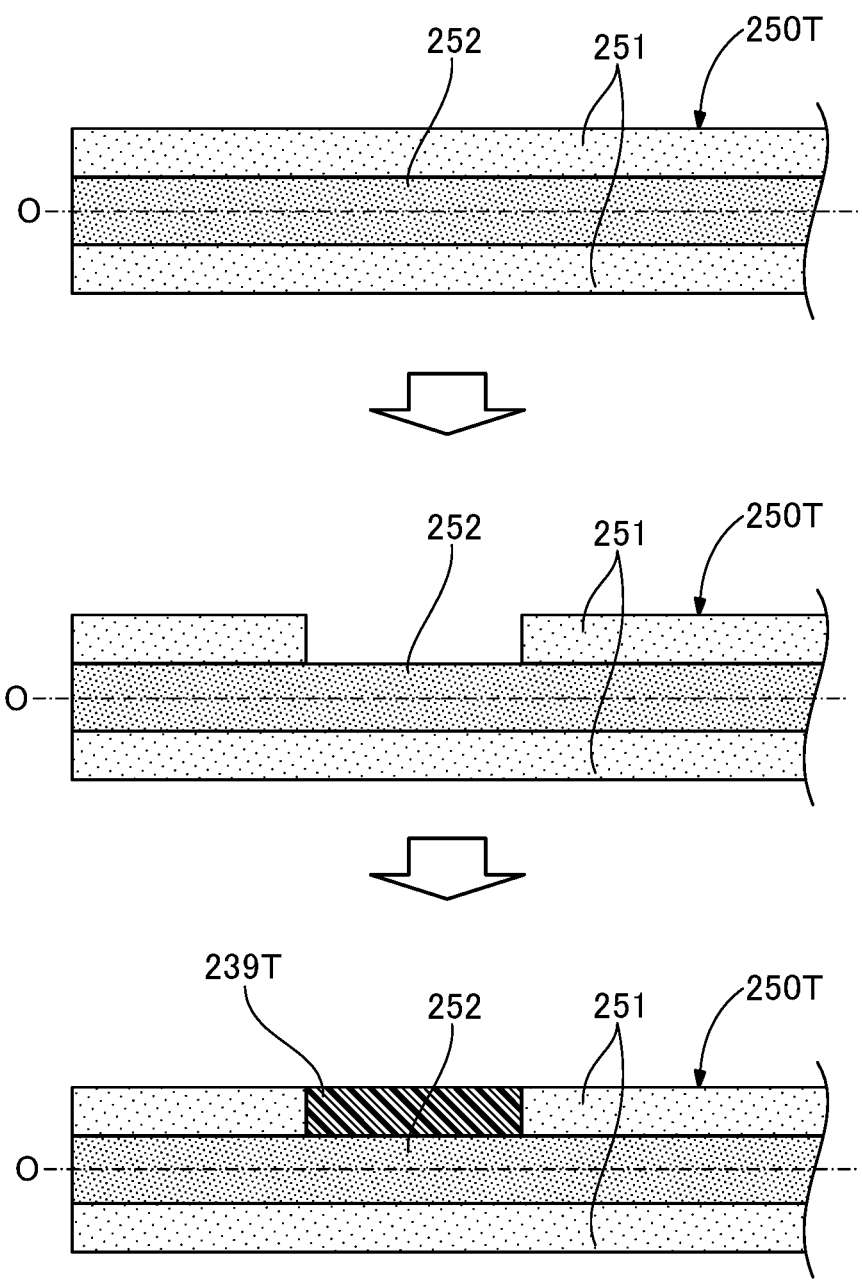
FIG. 29 is an explanatory diagram illustrating a method of forming a light irradiation portion.

FIG. 29 is an explanatory diagram illustrating a method of forming a light irradiation portion 239T. The light irradiation portion 239T formed partially in the circumferential direction may be used instead of the light irradiation portion 239S described above (FIGS. 27 and 28). First, in a side surface of a part of an optical fiber 250T on the distal end side, the clad 251 is removed partially in the circumferential direction. In the other part of the side surface, the clad 251 is not removed. Next, the part of the optical fiber 250T from which the clad 251 is removed is filled with a light-transmitting material (a resin or a metal). As a result, as illustrated in FIG. 29, the light irradiation portion 239T is formed in a part of the optical fiber 250T. It is noted that, for convenience of illustration, the clad 251 and the core 252 are only illustrated in FIGS. 28 and 29 and not in the other drawings (FIGS. 1 to 27).

Thus, various modifications can be applied to the light irradiation portions 239S and 239T, and the light irradiation portions 239S and 239T may include a light transmitting body that transmits the emission light LT from the core 252 exposed in a part of the optical fibers 250S and 250T on the distal end side. Further, the light irradiation portions 239S and 239T may be included in the light irradiation device 2 described in the first embodiment, or may be included in the light irradiation device 2N or the light irradiation device 2P described in the twelfth embodiment. According to the light irradiation systems using the light irradiation portions 239S and 239T of the thirteenth embodiment, an effect similar to the first embodiment described above can be achieved. Further, in the thirteenth embodiment, the light irradiation portions 239S and 239T can be easily formed by utilizing the optical fibers 250S and 250T. Further, the core 252 of the optical fibers 250S and 250T is covered with the light transmitting body (the light irradiation portions 239S and 239T), and thus, it is possible to suppress a decrease in the strength of the optical fibers 250S and 250T in the exposed part of the core 252.

Modifications of Embodiment

The disclosed embodiments are not limited to the above-described embodiments, and may be implemented in various modes without departing from the spirit of the disclosed embodiments. The following modifications can be applied, for example.

First Modification

In the first to thirteenth embodiments described above, examples of the configurations of the catheters 1 and 1A to 1M and the light irradiation devices 2, 2A, 2F, 2G, 2J, and 2N to 2S are illustrated. However, the configurations of the catheter 1 and the light irradiation device 2 can be modified in various ways. For example, a reinforcing layer formed of a braided body or a coil body may be embedded in the shaft 110 of the catheter 1 and the shaft 210 of the light irradiation device 2. Thus, it is possible to improve the torquability and the shape retention of the catheter 1 and the light irradiation device 2. For example, a coating formed by a hydrophilic or hydrophobic resin may be applied to the outer surface of the catheter 1 and the outer surface of the light irradiation device 2. Thus, the slidability of the catheter 1 in the living body lumen can be improved. Further, the slidability of the light irradiation device 2 in the lumen 110L of the catheter 1 can be improved. Moreover, the outer surface of the catheter 1 or the outer surface of the light irradiation device 2 may be coated with an antithrombotic material such as heparin. This makes it possible to suppress a decrease in laser output due to thrombus adhesion to the inner and outer surfaces of the catheter 1 and the outer surface of the light irradiation device 2 caused by the irradiation with the emission light (laser light) LT.

For example, the catheter 1 may include an expansion portion expandable in a radial direction (YZ-direction). For example, a balloon formed of a flexible thin film or a mesh body having wires arranged in a mesh shape can be used as the expansion portion. The expansion portion may be provided on at least one of the distal end side of the light transmitting portion 139 and the proximal end side of the light transmitting portion 139 in the shaft 110. Thus, after the catheter 1 is positioned in the living body lumen, the catheter 1 can be fixed in the living body lumen by expanding the expansion portion. Further, if a balloon is used as the expansion portion, the bloodstream at the site being irradiated with light can be blocked, and thus, it is possible to prevent that the bloodstream blocks the light.

For example, the catheter 1 may be configured as a multi-lumen catheter including a plurality of lumens different from the lumen 110L. Similarly, the light irradiation device 2 may be configured as a multi-lumen catheter including a separate lumen different from the lumen 210L into which the optical fiber 250 is inserted. In this case, the shaft 210 can be made using a hollow member having a substantially cylindrical shape, and the distal tip 220 can be provided with a through-hole extending along the direction of the axis O.

For example, the inner surface 120i of the distal tip 120 of the catheter 1 and the outer surface of the distal tip 220 of the light irradiation device 2 may be formed of a magnetic material and may be configured to attract each other. Thus, as illustrated in FIG. 5, a state where the light irradiation device 2 is inserted into the catheter 1 and the distal tip 220 is pressed against the distal tip 120 can be easily maintained.

Second Modification

In the first to thirteenth embodiments described above, examples of the configurations of the light transmitting portions 139, 139A to 139D, and 139K to 139M, and the light irradiation portions 239, 239A, and 239N to 239T are illustrated. However, the configurations of the light transmitting portions 139, 139A to 139D, and 139K to 139M, and the light irradiation portions 239, 239A, and 239N to 239T can be modified in various ways. For example, the light transmitting portion 139 may be formed of a radiopaque material, to integrally form the light transmitting portion 139 and the first marker portions 131 and 132. Similarly, the light irradiation portion 239 may be formed of a radiopaque material, to integrally form the light irradiation portion 239 and the second marker portions 231 and 232.

Third Modification

The configurations of the catheters 1 and 1A to 1M and the light irradiation devices 2, 2A, 2F, 2G, 2J, and 2N to 2S of the first to thirteenth embodiments, and the configurations of the catheters 1 and 1A to 1M and the light irradiation devices 2, 2A, 2F, 2G, 2J, and 2N to 2S of the first and second modifications described above may be appropriately combined. For example, in the catheter 1 and the light irradiation device 2 employing various combinations of the light transmitting portion 139 and the light irradiation portion 239 described in the second embodiment (FIG. 9), a configuration including a plurality of sets of the light transmitting portion 139 and the first marker portions 131 and 132 described in the third embodiment may be employed, the light transmitting portion 139 having the structure described in the fourth and fifth embodiments may be employed, the temperature sensor 180 described in the sixth embodiment may be provided, the first and second marker portions described in the seventh to tenth embodiments may be employed, the catheter described in the eleventh embodiment may be employed, and the light irradiation device described in the twelfth embodiment may be employed.

Although the aspects have been described based on the embodiments and the modifications, the embodiments of the above-described aspects are for facilitating understanding of the aspects, and do not limit the aspects. The aspects can be modified and improved without departing from the spirit of the aspects and the scope of the claims, and equivalent aspects are included in the aspects. Further, unless a technical feature is described as essential in the present specification, the technical feature may be omitted as appropriate.

DESCRIPTION OF REFERENCE NUMERALS 1, 1A to 1M . . . Catheter
2, 2A, 2F, 2G, 2J, 2N to 2S . . . Light irradiation device
3 . . . Laser light generator
110 . . . Shaft
120, 120J . . . Distal tip
131, 132 . . . First marker portion
139, 139A to 139D, 139K to 139M . . . Light transmitting portion
140 . . . Connector
141 . . . Connection portion
142 . . . Blade
161 . . . Marker
180 . . . Temperature sensor
210 . . . Shaft
220, 220J . . . Distal tip
231, 232 . . . Second marker portion
239, 239A, 239N to 239T . . . Light irradiation portion
240 . . . Connector
241 . . . Connection portion
242 . . . Blade
250 . . . Optical fiber

What is claimed is:

1. A light irradiation system for medical use, the light irradiation system comprising:
   a catheter having an elongated tube shape; and
   a light irradiation device having an elongated shape and configured to be inserted into the catheter, wherein
   the catheter includes:
      a light transmitting portion provided at least in a part of a side surface on a distal end side of the catheter and configured to transmit light inside the catheter to outside of the catheter;
      a first marker portion being radiopaque and being provided close to the light transmitting portion, the first marker portion indicating a position of the light transmitting portion; and
      a distal tip joined to the distal end side of the catheter, and
   the light irradiation device includes:
      a light irradiation portion provided at least in a part of a side surface on a distal end side of the light irradiation device and configured to output irradiation light to the outside; and
      a second marker portion being radiopaque and being provided close to the light irradiation portion, wherein the distal tip is formed with a through-hole penetrating the distal tip in an axial direction of the catheter and having a diameter smaller than an outer diameter of the light irradiation device, and when the light irradiation device is inserted into the catheter and a distal end of the light irradiation device abuts against an inner surface of the distal tip at which the through-hole is formed, the light irradiation portion and the light transmitting portion are aligned in an axial direction of the light irradiation system.

2. The light irradiation system according to claim 1, wherein
the first marker portion is provided at at least a first location on a distal end side and a second location on a proximal end side of the light transmitting portion in the axial direction of the catheter.

3. The light irradiation system according to claim 2, wherein
the second marker portion is provided at at least a first location on a distal end side and a second location on a proximal end side of the light irradiation portion in an axial direction of the light irradiation device.

4. The light irradiation system according to claim 3, wherein
in a state where the light irradiation device is inserted into the catheter and the light transmitting portion is aligned with the light irradiation portion in the axial direction of the light irradiation system,
the first marker portion at the distal end side is distal relative to the second marker portion at the distal end side, in the axial direction of the light irradiation system, and
the first marker portion at the proximal end side is proximal relative to the second marker portion at the proximal end side, in the axial direction of the light irradiation system.

5. The light irradiation system according to claim 2, wherein
the first marker portion has a shape surrounding the catheter in a circumferential direction, and
the second marker portion has a shape surrounding the light irradiation device in a circumferential direction.

6. The light irradiation system according to claim 2, wherein
a plurality of sets of the light transmitting portion and the first marker portion are provided in the catheter in the axial direction of the catheter.

7. The light irradiation system according to claim 2, wherein
the catheter further includes a temperature sensor configured to measure a temperature at least in a vicinity of the light transmitting portion.

8. The light irradiation system according to claim 2, wherein
the light irradiation portion is a light transmitting body configured to transmit emission light from a core exposed in a part of an optical fiber on the distal end side of the light irradiation device.

9. The light irradiation system according to claim 1, wherein the second marker portion is provided at at least a first location on a distal end side and a second location on a proximal end side of the light irradiation portion in an axial direction of the light irradiation device.

10. The light irradiation system according to claim 9, wherein
the first marker portion is provided at at least a first location on a distal end side and a second location on a proximal end side of the light transmitting portion in the axial direction of the catheter, and
in a state where the light irradiation device is inserted into the catheter and the light transmitting portion is aligned with the light irradiation portion in the axial direction of the light irradiation system,
the first marker portion at the distal end side is distal relative to the second marker portion at the distal end side, in the axial direction of the light irradiation system, and
the first marker portion at the proximal end side is proximal relative to the second marker portion at the proximal end side, in the axial direction of the light irradiation system.

11. The light irradiation system according to claim 1, wherein
the first marker portion has a shape surrounding the catheter in a circumferential direction, and
the second marker portion has a shape surrounding the light irradiation device in a circumferential direction.

12. The light irradiation system according to claim 1, wherein
a plurality of sets of the light transmitting portion and the first marker portion are provided in the catheter in the axial direction of the catheter.

13. The light irradiation system according to claim 1, wherein
the catheter further includes a temperature sensor configured to measure a temperature at least in a vicinity of the light transmitting portion.

14. The light irradiation system according to claim 1, wherein
the light irradiation portion is a light transmitting body configured to transmit emission light from a core exposed in a part of an optical fiber on the distal end side of the light irradiation device.

15. The light irradiation system according to claim 1, wherein
the light transmitting portion has a shape entirely surrounding the catheter in a circumferential direction, and
the light irradiation portion has a shape partially surrounding the light irradiation device in a circumferential direction.

16. The light irradiation system according to claim 1, wherein
the light transmitting portion has a shape partially surrounding the catheter in a circumferential direction, and
the light irradiation portion has a shape entirely surrounding the light irradiation device in a circumferential direction.

* * * * *